United States Patent [19]

Doria et al.

[11] Patent Number: 5,691,334
[45] Date of Patent: Nov. 25, 1997

[54] PYRROLYDENEMETHYL-DERIVATIVES AND PROCESS FOR THEIR PREPARATION

[75] Inventors: Gianfederico Doria, Milan; AnnaMaria Isetta, Rho Milan; Marcellino Tibolla, Senago Milan; MariaChiara Fornasiero, Vigevano Pavia; Mario Ferrari, Milan; Domenico Trizio, Cassina Rizzardi Como, all of Italy

[73] Assignee: Pharmacia & Upjohn S.p.A., Milan, Italy

[21] Appl. No.: 505,292

[22] PCT Filed: Dec. 2, 1994

[86] PCT No.: PCT/EP94/04006

§ 371 Date: Aug. 21, 1995

§ 102(e) Date: Aug. 21, 1995

[87] PCT Pub. No.: WO95/17381

PCT Pub. Date: Jun. 29, 1995

[30] Foreign Application Priority Data

Dec. 23, 1993 [GB] United Kingdom ............... 9326284

[51] Int. Cl.$^6$ .................. A61K 31/40; A61K 31/535; C07D 403/14; C07D 413/14
[52] U.S. Cl. ................. 514/235.5; 514/235.2; 514/414; 514/422; 544/141; 544/142; 548/468; 548/524
[58] Field of Search ................ 514/422, 414, 514/235.5, 235.2; 548/524, 468; 544/141, 142

[56] References Cited

PUBLICATIONS

JO 2250–828–A, Immunosuppressive... prodiginine, 1989.
J6 1280–429–A, Immunosuppressant... prodigiosin, 1985.
Patent Abstracts of Japan, vol. 11, No. 139, JP,P,61 280 429, 1987.

Annals of the New York Academy of Science, Immunomodulating Drugs, vol. 685, 1993, pp. 339–340.

Transplantation, vol. 47, No. 6, Jun. 1989.

Journal of Organic Chemistry, vol. 53, No. 7, 1988, pp. 1405–1415.

Journal of the Chemical Society Perkin Transactions 1, No. 3, 1986, pp. 455–463.

Journal of Organic Chemistry, vol. 35, No. 1, 1970, pp. 142–146.

CA 72: 43330, 2,2'-Bi–1H–pyrrole . . . 4–methoxy, p.15, 1971.

CA 83: 27050s Carbon–13 ... of label. p.418, Cushley et al, 1975.

CA 84: 176401e Prodigiosin ... species. Gandhi et al., p. 272, 1976.

CA 114: 183407c Selective ... prodigiosin 25–C. Nagai et al., p.594, 1991.

CA 115: 249975r Influence ... marcescens. Blessing et al., p. 266, 1991.

CA 123: 339718d Preparation ... activity. Doria et al., p. 1140, 1995.

*Primary Examiner*—Joseph McKane
*Attorney, Agent, or Firm*—Nikaido, Marmelstein, Murray & Oram LLP

[57] ABSTRACT

New and known 5-[(2H-pyrrol-2-ylidene)methyl]-2,2'-bi-1H-pyrrole derivatives, having immunomodulating activity and, represented by the general formula (I) and the pharmaceutically acceptable salts thereof, are disclosed.

40 Claims, No Drawings

PYRROLYDENEMETHYL-DERIVATIVES AND PROCESS FOR THEIR PREPARATION

This application is a 371 of PCT/EP94/04006 filed Dec. 2, 1994.

The present invention relates to new pyrrolydenemethyl-derivatives, to the use of known and new pyrrolydenemethyl-derivatives as therapeutic agents, in particular as immunomodulating agents, to a process for their preparation and to pharmaceutical compositions comprising them.

In literature several pyrrolydenemethyl-derivatives are known, for instance those disclosed by J. Antibiotics 24, 636 (1971); Mar. Biol. 34, 223 (1976); Can. J. Microbiol. 22. 658 (1976); Can. J. Chem. 56, 1155 (1978); Tetrahedron Letters 24 2797 (1983); J. Antibiotics 38, 128 (1985); J. Gen. Microbiol. 132, 1899 (1986); J. Antibiotics 28, 194 (1975), Nature 213, 903 (1967); Tetrahedron Letters 24, 2701 (1983); J. Antibiotics 39, 1155 (1986), J6 1280 429-A and JO 2250 828-A.

Most of the above reference relates to pyrrolydenemethyl-derivatives having anti-bacterial, antibiotic, antimicrobial and/or cytotoxic activity. Only few of them disclose immunosuppressive prodigiosine derivatives.

Object of the present invention are new 5-[(2H-pyrrol-2-ylidene)methyl]-2,2'-bi-1H-pyrrole derivatives having the following formula (I)

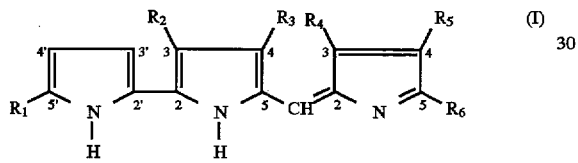

wherein
- $R_1$ represents hydrogen, phenyl, $C_1$–$C_{20}$ alkyl or $C_2$–$C_{20}$ alkenyl, wherein the alkyl and alkenyl groups may be unsubstituted or substituted by 1 to 3 substituents chosen independently from halogen, $C_1$–$C_6$ alkoxy, hydroxy, aryl and aryloxy;
- $R_2$ represents hydrogen, $C_1$–$C_6$ alkyl, cyano, carboxy or ($C_1$–$C_6$ alkoxy)carbonyl;
- $R_3$ represents halogen, hydroxy or $C_1$–$C_{11}$ alkoxy unsubstituted or substituted by phenyl;
- $R_4$ represent hydrogen, $C_1$–$C_6$ alkyl or phenyl; each or $R_5$ and $R_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups may be unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkylcarbamoyl, arylcarbamoyl and —$CON_cR_d$ in which each of $R_c$ and $R_d$ independently is hydrogen or $C_1$–$C_6$ alkyl or $R_c$ and $R_d$, taken together with the nitrogen atom to which they are linked, form a morpholino or piperidino ring; or two of $R_4$, $R_5$ and $R_6$ taken together form a $C_4$–$C_{12}$ polymethylene chain, which can be unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups may be in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl;

and the pharmaceutically acceptable salts thereof; and wherein
- when at the same time $R_3$ is methoxy and $R_1$, $R_2$, $R_4$ and $R_5$ are hydrogen, then $R_6$ is other than hydrogen, n-nonyl or n-undecyl; and wherein
- when at the same time $R_3$ is methoxy and $R_1$, $R_2$, $R_4$ and $R_6$ are hydrogen, then $R_5$ is other than n-undecyl; and wherein
- when at the same time $R_3$ is methoxy, and $R_1$ and $R_2$ are hydrogen, and $R_4$ and $R_6$ are methyl, then $R_5$ is other than hydrogen or ethyl; and wherein
- when at the same time $R_3$ is methoxy and $R_1$, $R_2$ and $R_5$, are hydrogen, then $R_4$ and $R_5$, taken together, are other than an α-ethyl-nonamethylene or α-butyl-heptamethylene chain; and wherein
- when at the same time $R_3$ is methoxy, $R_6$ is methyl and $R_1$, $R_2$ and $R_4$ are hydrogen, then $R_5$ is other than n-pentyl, n-hexyl, n-heptyl or n-undecyl; and wherein
- when at the same time $R_3$ is methoxy and $R_1$, $R_2$ and $R_4$ are hydrogen, then $R_5$ and $R_6$, taken together, are other than an α-butyl-heptamethylene chain; or $R_5$ being methyl, then $R_6$ is other than n-pentyl; or $R_5$ being ethyl, then $R_6$ is other than n-butyl; and wherein
- when at the same time $R_3$ is hydroxy, $R_1$, $R_2$ and $R_4$ are hydrogen and $R_6$ is methyl, then $R_5$ is other than n-pentyl; and wherein
- when at the same time $R_3$ is methoxy, $R_1$ and $R_2$ are hydrogen and $R_6$ is methyl, then $R_4$ and $R_5$, taken together, are other than an α-methyl-tetramethylene or β-methyl-tetramethylene chain; or $R_4$ being n-propyl, then $R_5$ is other than n-heptyl.

The present invention includes within its scope all possible isomers, stereoisomers and optical isomers and their mixtures, and the metabolites and the metabolic precursors or bioprecursors of the compounds of formula (I).

The compounds of the invention can be represented also by the following tautomeric formula (Ia)

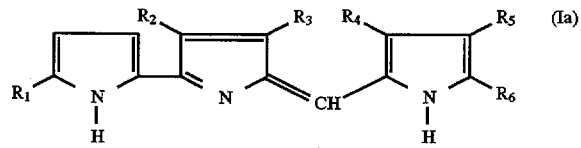

wherein $R_1$, $R_2$, $R_3$, $R_4$, $R_5$ and $R_6$ are as defined above.

Accordingly, the chemical compounds provided by the present invention are named throughout the description of the invention according to the chemical nomenclature provided for the compounds of either formula (I) or (Ia), on the basis of the structural evidence validated by people skilled in the art.

A halogen atom is preferably chlorine or fluorine. The alkyl, alkoxy, alkenyl, alkanoyl, alkenoyl, alkadienoyl and alkylidene groups may be branched or straight chain groups.

An aryl group as a substituent as well as a moiety in an aryloxy, aralkyl or arylcarbamoyl group is, e.g., an aromatic $C_6$–$C_{20}$ mono- or poly-nuclear moiety, typically phenyl, unsubstituted or substituted by one or two substituents independently chosen from halogen, hydroxy, $C_1$–$C_6$ alkyl and $C_1$–$C_6$ alkoxy.

Accordingly an aralkyl group is e.g. benzyl or phenethyl, in which the phenyl ring is optionally substituted by one or two substituents independently chosen from halogen, hydroxy, $C_1$–$C_6$ alkyl and $C_1$–$C_6$ alkoxy.

A $C_4$–$C_{12}$ polymethylene chain is e.g. a $C_4$–$C_9$ polymethylene chain.

A $C_3$–$C_4$ or $C_3$–$C_6$ alkenyl group is preferably an allyl group.

A $C_1$–$C_6$ alkyl group is preferably a $C_1$–$C_4$ alkyl group, in particular a methyl or ethyl group.

A $C_1$–$C_{12}$ alkyl group is preferably a $C_1$–$C_6$ alkyl group.

An unsubstituted $C_1$–$C_{11}$ alkoxy group is preferably a $C_1$–$C_4$ alkoxy or $C_8$–$C_{11}$ alkoxy group, typically methoxy, ethoxy, propoxy, butoxy and undecyloxy.

A $C_1$–$C_6$ alkoxy group substituted by phenyl is preferably a phenyl-$C_1$–$C_4$ alkoxy group, typically benzyloxy or phenylethoxy.

A $C_1$–$C_{20}$ alkyl group is preferably a $C_5$–$C_{14}$ alkyl group, in particular an undecyl group.

A $C_2$–$C_{20}$ alkenyl group is preferably a $C_5$–$C_{14}$ alkenyl group, in particular an undecenyl group.

A $C_2$–$C_{20}$ alkanoyl group is preferably a $C_5$–$C_{14}$ alkanoyl group, in particular an undecanoyl group.

A $C_3$–$C_{20}$ alkenoyl group is preferably a $C_5$–$C_{14}$ alkenoyl group, in particular an undecenoyl group.

A $C_1$–$C_{12}$ alkylidene group is preferably a $C_1$–$C_8$ alkylidene group, in particular a $C_4$–$C_6$ alkylidene group.

A $C_2$–$C_{12}$ alkenyl group is preferably a $C_3$–$C_6$ alkenyl group.

A ($C_1$–$C_6$ alkoxy)carbonyl group is preferably a ($C_1$–$C_4$ alkoxy)carbonyl group.

Examples of pharmaceutically acceptable salts are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethane-sulphonic acids.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are the compounds of formula (I) wherein, subjected to the above provisos, $R_1$ represents hydrogen, $C_1$–$C_{12}$ alkyl or $C_2$–$C_{12}$ alkenyl, wherein the alkyl and the alkenyl groups may be unsubstituted or substituted by aryl or aryloxy;

$R_2$ represents hydrogen, cyano, carboxy or ($C_1$–$C_4$ alkoxy)carbonyl;

$R_3$ represents hydroxy or $C_1$–$C_{11}$ alkoxy unsubstituted or substituted by phenyl;

$R_4$ represents hydrogen or $C_1$–$C_4$ alkyl; each of $R_5$ and $R_6$ independently represents hydrogen, $C_3$–$C_{14}$ alkyl or $C_3$–$C_{14}$ alkenyl, wherein the alkyl and the alkenyl groups may be unsubstituted or substituted by a substituent chosen from halogen, $C_1$–$C_4$ alkoxy, hydroxy, aryl, aryloxy, cyano, carboxy, ($C_1$–$C_4$alkoxy)carbonyl, aralkylcarbamoyl, arylcarbamoyl and —$CONR_cR_d$ in which each of $R_c$ and $R_d$ independently is hydrogen or $C_1$–$C_4$ alkyl or $R_c$ and $R_d$, taken together with the nitrogen atom to which they are linked, form a morpholino or piperidino ring; or two of $R_4$, $R_5$ and $R_6$ taken together form a $C_4$–$C_9$ polymethylene chain, which can be unsubstituted or substituted by a $C_1$–$C_6$ alkyl, by a $C_3$–$C_6$ alkenyl or by a $C_1$–$C_8$ alkylidene group, wherein the alkyl, alkenyl and alkylidene groups may be in turn unsubstituted or substituted by a substituent chosen from halogen, $C_1$–$C_4$ alkoxy, hydroxy, cyano, carboxy, ($C_1$–$C_4$ alkoxy)carbonyl, aryloxy and aryl; the remaining one being hydrogen or $C_1$–$C_6$ alkyl; and the pharmaceutically acceptable salts thereof.

Examples of particularly preferred compounds of the invention are:

4-methoxy-5-{[5-(undec-10-en-1-yl)-2H-pyrrol-2-ylidene]methyl}-2,2'-bi-1H-pyrrole;

4-ethoxy-5-[(5-decyl-2H-pyrrol-2-ylidene)methyl]-2,2,'-bi-1H-pyrrole;

4-ethoxy-5-[(5-dodecyl-2H-pyrrol-2-ylidene)methyl]-2,2'-bi-1H-pyrrole;

4-ethoxy-5-[(3,5-nonamethylene-2H-pyrrol-2-ylidene)methyl]-2,2'-bi-1H-pyrrole;

4-ethoxy-5-[(5-undecyl-2H-pyrrol-2-ylidene)methyl]-2,2'-bi-1H-pyrrole;

4-propoxy-5-[(5-undecyl-2H-pyrrol-2-ylidene)-methyl]-2,2'-bi-1H-pyrrole;

4-ethoxy-5-{[5-(undec-10-en-1-yl)-2H-pyrrol-2-ylidene]methyl}-2,2'-bi-1H-pyrrole;

4-isopropoxy-5-[(5-undecyl-2H-pyrrol-2-ylidene)methyl]-2,2'-bi-1H-pyrrole;

4-amyloxy-5-[(5-undecyl-2H-pyrrol-2-ylidene)methyl]-2,2'-bi-1H-pyrrole;

4-undecyloxy-5-[(5-undecyl-2H-pyrrol-2-ylidene)methyl]-2,2'-bi-1H-pyrrole;

4-benzyloxy-5-[(5-undecyl-2H-pyrrol-2-ylidene)methyl]-2,2'-bi-1H-pyrrole;

4-benzyloxy-5-[(2H-pyrrol-2-ylidene)methyl]-2,2'-bi-1H-pyrrole;

4-undecyloxy-5-[(2H-pyrrol-2-ylidene)methyl]-2,2'-bi-1H-pyrrole;

4-methoxy-5-[(5-tridecyl-2H-pyrrol-2-ylidene)methyl]-2,2'-bi-1H-pyrrole;

4-ethoxy-5-[(5-tridecyl-2H-pyrrol-2-ylidene)methyl]-2,2'-bi-1H-pyrrole;

4-buthoxy-5-[(5-tridecyl-2H-pyrrol-2-ylidene)methyl]-2,2'-bi-1H-pyrrole;

4-benzyloxy-5-[(5-tridecyl-2H-pyrrol-2-ylidene)methyl]-2,2'-bi-1H-pyrrole;

4-methoxy-5-[[5-(5-phenoxy-pent-1-yl)-2H-pyrrol-2-ylidene]methyl]-2,2'-bi-1H-pyrrole;

4-ethoxy-5-[[5-(5-phenoxy-pent-1-yl)-2H-pyrrol-2-ylidene]methyl]-2,2'-bi-1H-pyrrole;

4-buthoxy-5-[[5-(5-phenoxy-pent-1-yl)-2H-pyrrol-2-ylidene]methyl]-2,2'-bi-1H-pyrrole;

4-benzyloxy-5-[[5-(5-phenoxy-pent-1-yl)-2H-pyrrol-2-ylidene]methyl]-2,2'-bi-1H-pyrrole;

4-methoxy-5-[[5-(6-fluoro-hex-1-yl)-2H-pyrrol-2-ylidene]methyl]-2,2'-bi-1H-pyrrole;

4-methoxy-5-[[5-(6-hydoxy-hex-1-yl)-2H-pyrrol-2-ylidene]methyl]-2,2'-bi-1H-pyrrole;

4-methoxy-5-[[5-(5-morpholinecarboxamido-pent-1-yl)-2H-pyrrol-2-ylidene]methyl]-2,2'-bi-1H-pyrrole; and 4-methoxy-5-[[5-(7-cyano-hept-1-yl)-2H-pyrrol-2-ylidene]methyl]-2,2'-bi-1H-pyrrole;

and the pharmaceutically acceptable salts thereof, in particular the hydrochlorides, hydrobromides and methane-sulfonates.

A further object of the present invention is to provide a compound of formula (IB)

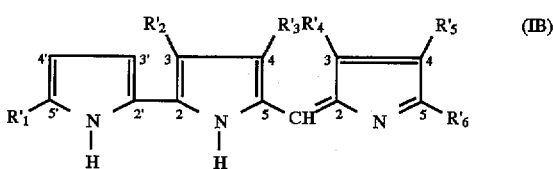

(IB)

wherein

R'₁ represents hydrogen, phenyl, C₁–C₂₀ alkyl or C₂–C₂₀ alkenyl, wherein the alkyl and alkenyl groups may be unsubstituted or substituted by 1 to 3 substituents chosen independently from halogen, C₁–C₆ alkoxy, hydroxy, aryl and aryloxy;

R'₂ represents hydrogen, C₁–C₆ alkyl, cyano, carboxy or (C₁–C₆ alkoxy)carbonyl;

R'₃ represents halogen, hydroxy or C₁–C₁₁ alkoxy unsubstituted or substituted by phenyl;

R'₄ represents hydrogen, C₁–C₆ alkyl or phenyl; each or R'₅ and R'₆ independently represents hydrogen, C₂–C₂₀ alkanoyl, C₃–C₂₀ alkenoyl, phenyl, C₁–C₂₀ alkyl or C₂–C₂₀ alkenyl, wherein the alkanoyl, alkenoyl, alkyl and the alkenyl groups may be unsubstituted or substituted by 1 to 3 substituents chosen independently from halogen, C₁–C₆ alkoxy, hydroxy, aryl, aryloxy, cyano, carboxy, (C₁–C₆ alkoxy)carbonyl, (C₃–C₄ alkenyl)carbamoyl, aralkylcarbamoyl, arylcarbamoyl and —CONR_cR_d in which each of R_c and R_d independently is hydrogen or C₁–C₆ alkyl or R_c and R_d, taken together with the nitrogen atom to which they are linked, form a morpholino or piperidino ring; or two of R'₄, R'₅ and R'₆ taken together form a C₄–C₁₂ polymethylene chain, which can be unsubstituted or substituted by a C₁–C₁₂ alkyl, by a C₂–C₁₂ alkenyl or by a C₁–C₁₂ alkylidene group, wherein the alkyl, alkenyl and alkylidene groups may be in turn unsubstituted or substituted by a substituent chosen from halogen, C₁–C₆ alkoxy, hydroxy, cyano, carboxy, (C₁–C₆ alkoxy)carbonyl, aryloxy and aryl; the remaining one being hydrogen or C₁–C₁₂ alkyl; or a pharmaceutically acceptable salt thereof; and wherein when at the same time R'₃ is methoxy and R'₁, R'₂, R'₄ and R'₅ are hydrogen, then R'₆ is other than n-nonyl or n-undecyl; and wherein when at the same time R'₃ is methoxy and R'₁, R'₂ and R'₅ are hydrogen, then R'₄ and R'₆, taken together, are other than an α-ethyl-nonamethylene chain; and wherein when at the same time R'₃ is methoxy, R'₆ is methyl and R'₁, R'₂ and R'₄ are hydrogen, then R'₅ is other than n-pentyl; and wherein when at the same time R'₃ is methoxy and R'₁, R'₂ and R'₄ are hydrogen, then R'₅ and R'₆, taken together, are other than an α-butyl-heptamethylene chain; and wherein when at the same time R'₃ is hydroxy, R'₁, R'₂ and R'₄ are hydrogen and R'₆ is methyl, then R'₅ is other than n-pentyl; and wherein when at the same time R'₃ is methoxy, R'₁ and R'₂ are hydrogen and R'₆ is methyl, then R'₄ and R'₅, taken together, are other than an α-methyl-tetramethylene chain; for use as a medicament, in particular as an immunomodulating agent, especially as an immunosuppressant agent.

Analogously to the compounds of formula (I) also the compounds of formula (IB) can be represented in tautomeric form as will be evident to those skilled in the art.

Preferred values of the substituents R'₁, R'₂, R'₃, R'₄, R'₅ and R'₆ occurring in formula (IB) are those mentioned above as to the corresponding substituents R₁ to R₆ occurring in formula (I).

Examples of pharmaceutically acceptable salts of a compound of formula (IB) are those mentioned above as to the compounds of formula (I).

Preferred compounds of formula (IB), as defined above, are those wherein, subject to the above provisos, R'₁ represents hydrogen, C₁–C₁₂ alkyl or C₂–C₁₂ alkenyl, wherein the alkyl and alkenyl groups may be unsubstituted or substituted by aryl or aryloxy;

R'₂ represents hydrogen, cyano, carboxy or (C₁–C₄ alkoxy)carbonyl;

R'₃ represents hydroxy or C₁–C₁₁ alkoxy unsubstituted or substituted by phenyl;

R'₄ represents hydrogen or C₁–C₄ alkyl; each or R'₅ and R'₆ independently represents hydrogen, C₃–C₁₄ alkyl or C₃–C₁₄ alkenyl, wherein the alkyl and the alkenyl groups may be unsubstituted or substituted by a substituent chosen from halogen, C₁–C₄ alkoxy, hydroxy, aryl, aryloxy, cyano, carboxy, (C₁–C₄ alkoxy)carbonyl, aralkylcarbamoyl, arylcarbamoyl and —CONR_cR_d in which each of R_c and R_d independently is hydrogen or C₁–C₄ alkyl or R_c and R_d, taken together with the nitrogen atom to which they are linked, form a morpholino or piperidino ring; or two of R'₄, R'₅ and R'₆ taken together form a C₄–C₉ polymethylene chain, which can be unsubstituted or substituted by a C₁–C₆ alkyl, by a C₃–C₆ alkenyl or by a C₁–C₈ alkylidene group, wherein the alkyl, alkenyl and alkylidene groups may be in turn unsubstituted or substituted by a substituent chosen from halogen, C₁–C₄ alkoxy, hydroxy, cyano, carboxy, (C₁–C₄ alkoxy)carbonyl, aryloxy and aryl; the remaining one being hydrogen or C₁–C₆ alkyl; and the pharmaceutically acceptable salts thereof.

Examples of specific compounds of formula (IB) are:

4-methoxy-5-{[5-(undec-10-en-1-yl)-2H-pyrrol-2-ylidene]methyl}-2,2'-bi-1H-pyrrole;
4-ethoxy-5-[(5-decyl-2H-pyrrol-2-ylidene)methyl]-2,2'-bi-1H-pyrrole;
4-ethoxy-5-[(5-dodecyl-2H-pyrrol-2-ylidene)methyl]-2,2'-bi-1H-pyrrole;
4-ethoxy-5-[(3,5-nonamethylene-2H-pyrrol-2-ylidene)methyl]-2,2'-bi-1H-pyrrole;
4-ethoxy-5-[(5-undecyl-2H-pyrrol-2-ylidene)methyl]-2,2'-bi-1H-pyrrole;
4-propoxy-5-[(5-undecyl-2H-pyrrol-2-ylidene)methyl]-2,2'-bi-1H-pyrrole;
4-ethoxy-5-{[5-(undec-10-en-1-yl)-2H-pyrrol-2-ylidene]methyl}-2,2'-bi-1H-pyrrole;
4-methoxy-5-[(4-ethyl-3,5-dimethyl-2H-pyrrol-2-ylidene)methyl]-2,2'-bi-1H-pyrrole;
4-methoxy-5-[(4-hexyl-5-methyl-2H-pyrrol-2-ylidene)methyl]-2,2'-bi-1H-pyrrole;
4-methoxy-5-[(5-methyl-4-undecyl-2H-pyrrol-2-ylidene)methyl]-2,2'-bi-1H-pyrrole;
4-isopropoxy-5-[(5-undecyl-2H-pyrrol-2-ylidene)methyl]-2,2'-bi-1H-pyrrole;
4-amyloxy-5-[(5-undecyl-2H-pyrrol-2-ylidene)methyl]-2,2'-bi-1H-pyrrole;
4-undecyloxy-5-[(5-undecyl-2H-pyrrol-2-ylidene)methyl]-2,2'-bi-1H-pyrrole;
4-benzyloxy-5-[(5-undecyl-2H-pyrrol-2-ylidene)methyl]-2,2'-bi-1H-pyrrole;
4-benzyloxy-5-[(2H-pyrrol-2-ylidene)methyl]-2,2'-bi-1H-pyrrole;
4-undecyloxy-5-[(2H-pyrrol-2-ylidene)methyl]-2,2'-bi-1H-pyrrole;
4-methoxy-5-[(5-tridecyl-2H-pyrrol-2-ylidene)methyl]-2,2'-bi-1H-pyrrole;

4-ethoxy-5-[(5-tridecyl-2H-pyrrol-2-ylidene)methyl]-2,2'-bi-1H-pyrrole;

4-buthoxy-5-[(5-tridecyl-2H-pyrrol-2-ylidene)methyl]-2,2'-bi-1H-pyrrole;

4-benzyloxy-5-[(5-tridecyl-2H-pyrrol-2-ylidene)methyl]-2,2'-bi-1H-pyrrole;

4-methoxy-5-[[5-(5-phenoxy-pent-1-yl)-2H-pyrrol-2-ylidene]methyl]-2,2'-bi-1H-pyrrole;

4-ethoxy-5-[[5-(5-phenoxy-pent-1-yl)-2H-pyrrol-2-ylidene]methyl]-2,2'-bi-1H-pyrrole;

4-buthoxy-5-[[5-(5-phenoxy-pent-1-yl)-2H-pyrrol-2-ylidene]methyl]-2,2'-bi-1H-pyrrole;

4-benzyloxy-5-[[5-(5-phenoxy-pent-1-yl)-2H-pyrrol-2-ylidene]methyl]-2,2'-bi-1H-pyrrole;

4-methoxy-5-[[5-(6-fluoro-hex-1-yl)-2H-pyrrol-2-ylidene]methyl]-2,2'-bi-1H-pyrrole;

4-methoxy-5-[[5-(6-hydoxy-hex-1-yl)-2H-pyrrol-2-ylidene]methyl]-2,2'-bi-1H-pyrrole;

4-methoxy-5-[[5-(5-morpholinecarboxamido-pent-1-yl)-2H-pyrrol-2-ylidene]methyl]-2,2'-bi-1H-pyrrole; and 4-methoxy-5-[[5-(7-cyano-hept-1-yl)-2H-pyrrol-2-ylidene]methyl]-2,2'-bi-1H-pyrrole;

and the pharmaceutically acceptable salts thereof, in particular the hydrochlorides, hydrobromides and methanesulfonates.

Object of the present invention is also to provide a pharmaceutical composition comprising a pharmaceutically acceptable carrier and/or diluent and as an active principle a compound of formula (I) or (IB) as herein defined, or a pharmaceutically acceptable salt thereof. The present invention also provides the use of a compound of formula (IC)

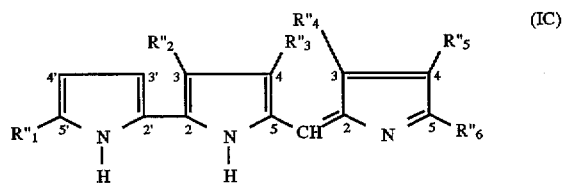

wherein $R''_1$ represents hydrogen, phenyl, $C_1$–$C_{20}$ alkyl or $C_2$–$C_{20}$ alkenyl, wherein the alkyl and alkenyl groups may be unsubstituted or substituted by 1 to 3 substituents chosen independently from halogen, $C_1$–$C_6$ alkoxy, hydroxy, aryl and aryloxy;

$R''_2$ represents hydrogen, $C_1$–$C_6$ alkyl, cyano, carboxy or ($C_1$–$C_6$ alkoxy)carbonyl;

$R''_3$ represents halogen, hydroxy or $C_1$–$C_{11}$ alkoxy unsubstituted or substituted by phenyl;

$R''_4$ represents hydrogen, $C_1$–$C_6$ alkyl or phenyl; each or $R''_5$ and $R''_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups may be unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkylcarbamoyl, arylcarbamoyl and —CONR$_c$R$_d$ in which each of R$_c$ and R$_d$ independently is hydrogen or $C_1$–$C_6$ alkyl or R$_c$ and R$_d$, taken together with the nitrogen atom to which they are linked, form a morpholino or piperidino ring; or two of $R''_4$, $R''_5$ and $R''_6$ taken together form a $C_4$–$C_{12}$ polymethylene chain, which can be unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups may be in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl;

and the pharmaceutically acceptable salts thereof; and wherein when at the same time $R''_3$ is methoxy and $R''_1$, $R''_2$, $R''_4$ and $R''_5$ are hydrogen, then $R''_6$ is other than n-undecyl; and wherein when at the same time $R''_3$ is methoxy and $R''_1$, $R''_2$ and $R''_5$ are hydrogen, then $R''_4$ and $R''_6$, taken together, are other than an α-ethyl-nonamethylene chain; and wherein when at the same time $R''_3$ is methoxy and $R''_1$, $R''_2$ and $R''_4$ are hydrogen, then $R''_5$ and $R''_6$, taken together, are other than an α-butyl-heptamethylene chain; in the preparation of a medicament having immunomodulating, in particular immunosuppressant, activity.

Accordingly, object of the present invention is also to provide a pharmaceutical composition comprising a pharmaceutically acceptable carrier and/or diluent and as an active principle a compound of formula (IC) as herein defined, or a pharmaceutically acceptable salt thereof, having immunomodulating, in particular immunosuppressant, activity.

Analogously to the compounds of formulae (I) and (IB), also the compounds of formula (IC) can be represented in tautomeric form as will be evident to those skilled in the art.

Preferred values of the substituents $R''_1$, $R''_2$, $R''_3$, $R''_4$, $R''_5$ and $R''_6$ occurring in formula (IC) are those mentioned above as to the corresponding substituents $R_1$ to $R_6$ occurring in formula (I).

Examples of pharmaceutically acceptable salts of a compound of formula (IC) are those mentioned above as to the compounds of formula (I).

Preferred compounds of formula (IC), as defined above, are those wherein, subject to the above provisos, $R''_1$ represents hydrogen, $C_1$–$C_{12}$ alkyl or $C_2$–$C_{12}$ alkenyl, wherein the alkyl and alkenyl groups may be unsubstituted or substituted by aryl or aryloxy;

$R''_2$ represents hydrogen, cyano, carboxy or ($C_1$–$C_4$ alkoxy)carbonyl;

$R''_3$ represents halogen, hydroxy or $C_1$–$C_4$ alkoxy unsubstituted or substituted by phenyl;

$R''_4$ represents hydrogen or $C_1$–$C_4$ alkyl;

each or $R''_5$ and $R''_6$ independently represents hydrogen, $C_3$–$C_{14}$ alkyl or $C_3$–$C_{14}$ alkenyl, wherein the alkyl and the alkenyl groups may be unsubstituted or substituted by a substituent chosen from halogen, $C_1$–$C_4$ alkoxy, hydroxy, aryl, aryloxy, cyano, carboxy, ($C_1$–$C_4$ alkoxy) carbonyl, aralkylcarbamoyl, arylcarbamoyl and —CONR$_c$R$_d$ wherein each of R$_c$ and R$_c$ independently is hydrogen or $C_1$–$C_4$ alkyl or R$_c$ and R$_d$, taken together form a morpholino or piperidino ring; or two of $R''_4$, $R''_5$ and $R''_6$ taken together form a $C_4$–$C_9$ polymethylene chain, which can be unsubstituted or substituted by a $C_1$–$C_6$ alkyl, by a $C_3$–$C_6$ alkenyl or by a $C_1$–$C_8$ alkylidene group, wherein the alkyl, alkenyl and alkylidene groups may be in turn unsubstituted or substituted by a substituent chosen from halogen, $C_1$–$C_4$ alkoxy, hydroxy, cyano, carboxy, ($C_1$–$C_4$ alkoxy) carbonyl, aryloxy and aryl; the remaining one being hydrogen or $C_1$–$C_6$ alkyl;

and the pharmaceutically acceptable salts thereof.

Examples of specific compounds of formula (IC) are:

4-methoxy-5-{[5-(undec-10-en-1-yl)-2H-pyrrol-2-ylidene] methyl}-2,2'-bi-1H-pyrrole;
4-ethoxy-5-[(5-decyl-2H-pyrrol-2-ylidene)methyl]-2,2,'-bi-1H-pyrrole;
4-ethoxy-5-[(5-dodecyl-2H-pyrrol-2-ylidene)methyl]-2,2,'-bi-1H-pyrrole;
4-ethoxy-5-[(3,5-nonamethylene-2H-pyrrol-2-ylidene) methyl]-2,2'-bi-1H-pyrrole;
4-ethoxy-5-[(5-undecyl-2H-pyrrol-2-ylidene)methyl]-2,2,'-bi-1H-pyrrole;
4-propoxy-5-[(5-undecyl-2H-pyrrol-2-ylidene)methyl]-2,2'-bi-1H-pyrrole;
4-ethoxy-5-{[5-(undec-10-en-1-yl)-2H-pyrrol-2-ylidene] methyl}-2,2'-bi-1H-pyrrole;
4-methoxy-5-[(4-ethyl-3,5-dimethyl-2H-pyrrol-2-ylidene) methyl]-2,2'-bi-1H-pyrrole;
4-methoxy-5-[(4-hexyl-5-methyl-2H-pyrrol-2-ylidene) methyl]-2,2'-bi-1H-pyrrole;
4-methoxy-5-[(5-methyl-4-undecyl-2H-pyrrol-2-ylidene) methyl]-2,2'-bi-1H-pyrrole;
4-methoxy-5-[(5-nonyl-2H-pyrrol-2-ylidene)methyl]-2,2'-bi-1H-pyrrole;
4-methoxy-5-[(5-methyl-4-pentyl-2H-pyrrol-2-ylidene) methyl]-2,2'-bi-1H-pyrrole;
4-isopropoxy-5-[(5-undecyl-2H-pyrrol-2-ylidene)methyl]-2,2'-bi-1H-pyrrole;
4-amyloxy-5-[(5-undecyl-2H-pyrrol-2-ylidene)methyl]-2,2'-bi-1H-pyrrole;
4-undecyloxy-5-[(5-undecyl-2H-pyrrol-2-ylidene)methyl]-2,2'-bi-1H-pyrrole;
4-benzyloxy-5-[(5-undecyl-2H-pyrrol-2-ylidene)methyl]-2,2'-bi-1H-pyrrole;
4-benzyloxy-5-[(2H-pyrrol-2-ylidene)methyl]-2,2'-bi-1H-pyrrole;
4-undecyloxy-5-[(2H-pyrrol-2-ylidene)methyl]-2,2'-bi-1H-pyrrole;
4-methoxy-5-[(5-tridecyl-2H-pyrrol-2-ylidene)methyl]-2,2'-bi-1H-pyrrole;
4-ethoxy-5-[(5-tridecyl-2H-pyrrol-2-ylidene)methyl]-2,2'-bi-1H-pyrrole;
4-buthoxy-5-[(5-tridecyl-2H-pyrrol-2-ylidene)methyl]-2,2'-bi-1H-pyrrole;
4-benzyloxy-5-[(5-tridecyl-2H-pyrrol-2-ylidene)methyl]-2,2'-bi-1H-pyrrole;
4-methoxy-5-[[5-(5-phenoxy-pent-1-yl)-2H-pyrrol-2-ylidene]methyl]-2,2'-bi-1H-pyrrole;
4-ethoxy-5-[[5-(5-phenoxy-pent-1-yl)-2H-pyrrol-2-ylidene] methyl]-2,2'-bi-1H-pyrrole;
4-buthoxy-5-[[5-(5-phenoxy-pent-1-yl)-2H-pyrrol-2-ylidene]methyl]-2,2'-bi-1H-pyrrole;
4-benzyloxy-5-[[5-(5-phenoxy-pent-1-yl)-2H-pyrrol-2-ylidene]methyl]-2,2'-bi-1H-pyrrole;
4-methoxy-5-[[5-(6-fluoro-hex-1-yl)-2H-pyrrol-2-ylidene] methyl]-2,2'-bi-1H-pyrrole;
4-methoxy-5-[[5-(6-hydoxy-hex-1-yl)-2H-pyrrol-2-ylidene] methyl]-2,2'-bi-1H-pyrrole;
4-methoxy-5-[[5-(5-morpholinecarboxamido-pent-1-yl)-2H-pyrrol-2-ylidene]methyl]-2,2'-bi-1H-pyrrole; and
4-methoxy-5-[[5-(7-cyano-hept-1-yl)-2H-pyrrol-2-ylidene] methyl]-2,2'-bi-1H-pyrrole;

and the pharmaceutically acceptable salts thereof, in particular the hydrochlorides, hydrobromides and methanesulfonates.

The new compounds of formula (I) and the known ones falling within formulae (IB) and (IC) and the pharmaceutically acceptable salts thereof can be obtained by the same analogy process.

According to a preferred embodiment of the invention a compound of formula (I) and the salts thereof can be prepared by a process comprising:

A) reacting a compound of formula (II)

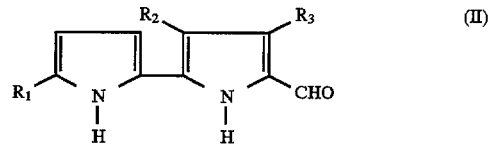

wherein
$R_1$, $R_2$ and $R_3$ are as defined above, with a compound of formula (III)

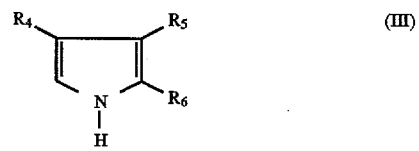

wherein
$R_4$, $R_5$ and $R_6$ are as defined above; or
B) reacting a compound of formula (IV)

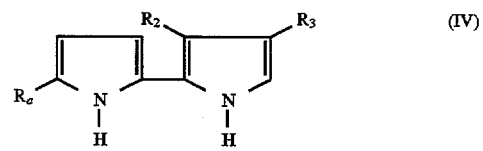

wherein
$R_a$ is as $R_1$ above except hydrogen and $R_2$ and $R_3$ are as defined above, with a compound of formula (V)

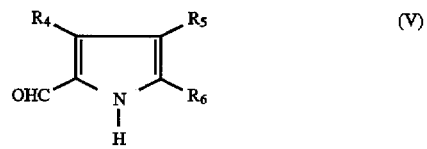

wherein
$R_4$, $R_5$ and $R_6$ are as defined above so obtaining a compound of formula (I) as defined above wherein $R_1$ is other than hydrogen; and, if desired, converting a compound of formula (I) into another compound of formula (I) and/or, if desired, converting a compound of formula (I) into a pharmaceutically acceptable salt and/or, if desired, converting a salt into a free compound and/or, if desired, separating a mixture of isomers of a compound of formula (I) into the single isomers.

The reaction between a compound of formula (II) and a compound of formula (III) as well as the reaction between a compound of formula (IV) and a compound of formula (V) may be carried out, for example, in an organic solvent such as a lower alkanol e.g. methanol or ethanol; tetrahydrofuran, ethyl acetate, dichloromethane or their mixtures, at a temperature varying between about 0° C. and the reflux temperature, in the presence of an inorganic acid such as hydrochloric, hydrobromic, methanesulfonic acid or $BF_3$.etherate, preferably in the absence of water.

A compound of formula (I) may be converted, as stated above, into another compound of formula (I) by known methods; for example, in a compound of formula (I) a carboxy group may be converted into the corresponding ($C_1$–$C_6$ alkyl)- or aryl-carbamoyl group by reaction with the suitable $C_1$–$C_6$ alkylamine or arylamine, respectively, in the presence of a suitable carbodiimide, such as dicyclohexylcarbodiimide or 1-(3-dimethylamino-propyl)-3-ethyl-carbodiimide, in an inert solvent such as dichloromethane or tetrahydrofuran at a temperature varying between about 0° C. and about 30° C.

Also the optional salification of a compound of formula (I) as well as the conversion of a salt into the free compound and the separation of a mixture of isomers into the single isomers may be carried out by conventional methods. For example, the separation of optical isomers may be carried out by salification with an optically active base or acid and by subsequent fractional crystallization of the diastereoisomeric salts, followed by recovering of the optically active isomeric acids or, respectively, bases.

The compounds of formula (II) may be prepared, for example, starting from a compound of formula (VI)

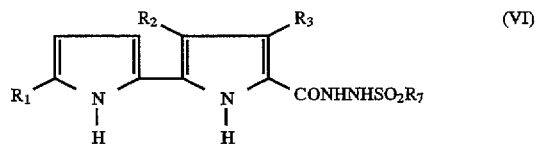

wherein $R_1$, $R_2$ and $R_3$ are as defined above and $R_7$ is aryl, in particular 4-methylphenyl or 2,4,6-triisopropylphenyl, by means of the well known McFadyen-Stevens synthesis of aldehydes from acyl-sulfonyl-hydrazides, according, for example, to the conventional procedure described in J. Org. Chem. 53, 1405 (1988) or to improved procedure described in J. Amer. Chem. Soc. 80, 862 (1958) and Tetrahedron Letters, 21, 4645 (1980).

Alternatively, the compounds of formula (II) wherein $R_1$ is other than hydrogen may be prepared, for example, by reacting a suitable compound of formula (IV) with a Vilsmeier reagent, according to well known chemical procedures, for example as described in J. Heter. Chem., 13, 497 (1976).

The compounds of formula (III) are known compounds or may be prepared by using mere variations of published procedures, for example those reported in the following chemical literature:

| Tetrahedron | 32, | 1851 | (1976); |
| Tetrahedron | 32, | 1867 | (1976); |
| Tetrahedron | 32, | 1863 | (1976); |
| Tetrahedron Letters | 25, | 1387 | (1984); |
| J. Org. Chem. | 53, | 1410 | (1988); |
| J. Org. Chem. | 28, | 857 | (1963); |
| J. Am. Chem. Soc. | 84, | 4655 | (1962); |
| Ann. | 450, | 181 | (1926); |
| Ber. | 99, | 1414 | (1966). |

The compounds of formula (IV), which are new and are further object of the present invention, may be synthesized, for example, by hydrolysis and decarboxylation of compounds of formula (VII)

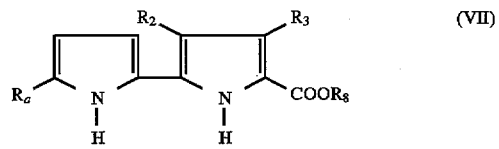

wherein $R_a$, $R_2$ and $R_3$ are as defined above and $R_8$ is $C_1$–$C_6$ alkyl, following, for example, the method described in J. Heter. Chem., 13. 197 (1976).

Alternatively the compounds of formula (IV) can be prepared by a method of synthesis, which is new and is a further object of the present invention, comprising the condensation of a compound of formula (VIII)

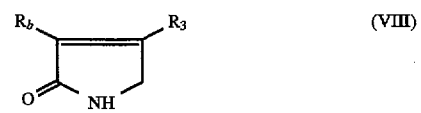

wherein $R_3$ is as defined above and $R_b$ is as $R_2$ defined above except carboxy, with a compound of formula (IX)

wherein $R_a$ is as defined above, so obtaining a compound of formula (IV) as defined above wherein $R_2$ is other than carboxy.

The condensation between a compound of formula (VIII) and a compound of formula (IX) can be performed e.g. by the action of $POCl_3$ in the absence of a solvent as well as in the presence of an inert organic solvent such as dichloromethane or dichloroethane, at a temperature varying between about 0° C. and about 50° C.

The compounds of formula (V), wherein $R_6$ is other than hydrogen, may be prepared, for example, by Vilsmeier formylation of the compounds of formula (III), wherein $R_6$ is other than hydrogen, according to a well known chemical procedure.

The compounds of formulae (VI) and (VII) may be prepared by using variations of published procedures, for example those reported in the following chemical literature:

| J. Org. Chem. | 53, | 1405 | (1988); |
| Tetrahedron Letters | 30, | 1725 | (1989); |
| Tetrahedron Letters | 26, | 2259 | (1977). |

When in the compounds of the present invention and in the intermediate products thereof, groups are present, such as COOH and/or OH, which need to be protected before submitting them to the hereabove illustrated reactions, they may be protected before the reactions take place and then deprotected, according to well known methods in organic chemistry.

The compounds of formulae (I), (IB), and (IC), and the pharmaceutically acceptable salts thereof are herein defined as the "compounds of the present invention", the "compounds of the invention" and/or the "active principles of the pharmaceutical compositions of the invention".

The compounds of the invention have immunomodulating, in particular immunosuppressant, activity as found in several biological tests.

For instance, the compounds of the present invention have been evaluated in comparison to the reference compound undecylprodigiosine (UP) on the following tests.

1. Proliferation of murine splenocytes induced by the mitogen Concanavaline A.
2. Proliferation of murine splenocytes induced by irradiated allogenic murine spleen cells (MLR).
3. Proliferation of tumor cell lines (human erythroleukemia K562, murine melanoma B16).

Tests 1 and 2 allow the study of the compounds on proliferation models mediated by T-cell growth factors (e.g. IL-2) and are considered immunologically specific.

Test 3 allows to investigate the inhibitory effect of the present compounds on a generic proliferation pathway, independent from immune-specific growth factors.

The tests have been carried out as follows:

Test n°1

Spleens were aseptically removed from C57B1/6 mice and a cell suspension prepared in complete medium. Cell viability was evaluated by trypan blue exclusion.

Spleen cells ($4\times10^5$) were cultured in triplicate in a volume of 0.15 ml, in flat bottomed microculture plates, in the absence or presence of an optimal concentration of ConA (1.7 microgr/ml) and of different concentrations of the test compound. Cultures were incubated for 72 h at 37° C. in a humidified, 5% $CO_2$ incubator; 18 h before termination of the cultures, 0.2 microCi of [methyl-$^3$H]thymidine were added to each well. Cells were harvested on glass fiber filters and the [$^3$H]TdR uptake (cpm) quantified in a liquid scintillation counter.

Test n°2

Spleens were aseptically removed from C57B1/6 mice (responders) and Balb/c mice (stimulators), and cell suspensions prepared in complete medium. Responder cells ($1\times10^6$) were cocultured in triplicate with irradiated (1500R) stimulator cells ($5\times10^5$) in a volume of 0.15 ml in the presence or absence of different concentrations of the test compound, in flat bottomed microculture plates. Cultures were incubated for 96 h at 37° C. in a humidified, 5% $CO_2$ incubator; the last 18 h in the presence of 0.2 microCi of $^3$H-TdR.

Cells were harvested on glass fiber filter and the $^3$H-TdR uptake (cpm) quantified in a liquid scintillation counter.

Test n°3

Tumor cells were collected in the logarithmic phase of growth and seeded in triplicate in flat bottomed microculture plates at the concentration of $1\times10^4$ in the presence or absence of different concentrations of the test compound. After 48 h incubation at 37° C. in 5% $CO_2$, the cell viability was evaluated by the MTT colorimetric method according to Ferrari et al., J. Immunol. Methods (1990) 131, 165–72.

The concentration inhibiting 50% (IC50) of the cell proliferation in the different settings is calculated for the test compounds and the reference standard UP. The ratio between the mean IC50 values on tumor cells growth (test 3) and the IC50 on lymphocytes proliferation (measured by test 1 and 2) produces the therapeutic index (TI) of the compounds.

The obtained test data are reported in the following table.

| Compound | IC50 ng/ml (upper and lower limits) | | | | TI |
|---|---|---|---|---|---|
| | lymphocyte prolifer. | | tumor cell growth | | |
| FCE 28512 | 2.3 | (1.5–3.4) | 510.6 | (267.1–1334.5) | 222 |
| FCE 28526 | 2.0 | (1.25–3.15) | 583.9 | (310.9–1426.8) | 290 |
| FCE 28733 | 5.1 | (3.6–7.3) | 858.6 | (437.7–2696.0) | 168 |
| FCE 28789 | 11.9 | (8.6–16.7) | 784.1 | (396.2–3246.5) | 66 |
| FCE 29002 | 30.1 | (22.5–40.2) | 5800 | (n.c.) | 193 |
| UP | 2.9 | (1.8–4.5) | 105.7 | (59.9–210.3) | 36 |

In the table, the reference compound UP is 4-methoxy-5-[(5-undecyl-2H-pyrrol-2-ylidene)methyl]-2,2'-bi-1H-pyrrole, hydrochloride.

FCE 28512 is 4-ethoxy-5-[(5-undecyl-2H-pyrrol-2-ylidene)methyl]-2,2'-bi-1H-pyrrole, hydrochloride.

FCE 28526 is 4-methoxy-5-[(5-tridecyl-2H-pyrrol-2-ylidene)methyl]-2,2'-bi-1H-pyrrole, hydrochloride.

FCE 28733 is 4-ethoxy-5-[(5-tridecyl-2H-pyrrol-2-ylidene)methyl]-2,2'-bi-1H-pyrrole, hydrochloride.

FCE 28789 is 4-buthoxy-5-[(5-undecyl-2H-pyrrol-2-ylidene)methyl]-2,2'-bi-1H-pyrrole, hydrochloride.

FCE 29002 is 4-benzyloxy-5-[(5-undecyl-2H-pyrrol-2-ylidene)methyl]-2,2'-bi-1H-pyrrole, hydrochloride.

These data demonstrate that the representative compounds of the invention are endowed with a considerably higher TI than that of the reference compound, therefore showing that their immunosuppressive effect is more specific for activated lymphocytes. Accordingly, the compounds of the present invention possess more valuable immunopharmacological properties than that of the natural reference compound undecylprodigiosine.

The compounds of the invention can therefore be used in mammals, including humans, as immunosuppressive agents for the prevention and treatment of rejection phenomena associated with tissue and organ transplantations, graft-versus-host diseases and autoimmune diseases. A human or animal may therefore be treated by a methods comprising the administration thereto of a therapeutically effective amount of a compound of the invention or a pharmaceutically acceptable salt thereof. The condition of the human or animal patient can thus be improved.

Preferred cases of organ and tissue transplants which can be successfully treated by the compounds of the invention, hereabove described, are, for example, the cases of heart, kidney and bone marrow transplantation. Preferred cases of autoimmune diseases which can be successfully treated by the compounds of the invention, hereabove described, are for example, the cases of rheumatoid arthritis, systemic lupus erythematosus, juvenile diabetes, autoimmune haemolytic anaemia, miastenia gravis, multiple sclerosis, psoriasis, ulcerative colitis, idiopathic thrombocytopenic purpura, active chronic hepatitis, glomerulonephritis, idiopathic leucopenia, primary biliary cirrhosis, thyroiditis, thyrotoxicosis, dermatomyositis, discoid lupus erythematosus, psoriatic arthritis, regional enteritis, nephrotic syndrome, lupus nephritis, lupoid hepatitis, Sjögren's syndrome, Goodpasture's syndrome, Wegener's granulomatosis, scleroderma, Sezary's disease, uveitis and mumps orchitis. Typically rheumatoid arthritis, systemic lupus erythematosus, juvenile diabetes, miastenia gravis, multiple sclerosis and psoriasis. The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the acute treatments.

For maintenance regimens the oral or parenteral, e.g. intramuscular or subcutaneous, route is preferred. For these purposes the compounds of the invention, e.g. FCE 28512, can be administered orally at doses ranging e.g. from about 1 to about 20 mg/kg of body weight per day in adult humans.

Doses of active compounds ranging e.g. from about 0.25 to about 5 mg/kg of body weight per day can be used for the parenteral administration and for intravenous injection or infusion in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention, may be administered in the form of aqueous or oily solutions or suspensions, tablets, pills, gelatine capsules, syrups, drops or suppositories.

Thus, for oral administration, the pharmaceutical compositions, containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixture; dyestuffs; sweeteners; wetting agents, such as lecithin, polysorbates, laurylsulphates and in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The present invention also provides products containing a compound of formula (IC), or a pharmaceutically acceptable salt thereof, and an additional drug as a combined preparation for simultaneous, separate or sequential use in immunosuppressant therapy in mammals. Such additional drug can be for instance a corticosteroid, an immunosuppressant or an anti-tumor agent, or mixtures of two or more of them.

The term "antitumor agent" is meant to comprise both a single anti-tumor drug and "cocktails", i.e a mixture of such drugs according to clinical practice.

Examples of anti-tumor agents that can be formulated with a compound of formula (IC), include methotrexate, mycophenolic acid and cyclophosphamide and mixtures thereof.

The term "immunosuppressant agent" is meant to comprise both a single immunosuppressant drug and "cocktails", i.e a mixture of such drugs according to clinical practice.

Examples of immunosuppressant agents that can be formulated with a compound of formula (IC), include cyclosporin A, FK506, rapamycin and azathioprine and mixtures thereof.

Similarly a preferred example of corticosteroids is dexametason.

The following examples illustrate but do not limit the invention:

EXAMPLE 1

3-Hydroxy-pyrrole-2-carboxylic acid ethyl ester (2.5 g), prepared according to Chem. Pharm. Bull. 26, 2228 (1978), dissolved in tetrahydrofuran (25 ml) is added dropwise under stirring at 25° C. to a suspension of 60% NaH (0.71 g) in tetrahydrofuran (25 ml). After the effervescence has ceased (about 30 minutes) diethylsulfate (3.16 ml) is added and the reaction mixture is kept under stirring at room temperature for 64 hours. The obtained solution is treated with 10% $NH_4OH$ for 10 minutes under stirring and then extracted with ethyl acetate, washed with brine and evaporated to dryness in vacuo.

The residue is purified over a flash column using toluene/ethyl acetate 8:2 as eluant, yielding 3.35 g of 3-ethoxy-pyrrole-2-carboxylic acid ethyl ester, m.p. 81°–83° C., which are dissolved in tetrahydrofuran (65 ml) and then added dropwise under stirring at 25°–30° C. to a suspension of 60% NaH (0.73 g); after 10 minutes the effervescence has ceased and the obtained solution is added dropwise under stirring at 20° C. to a solution of pyrrole-1-carboxylic acid anhydride prepared from pyrrole-1-carboxylic acid (4.05 g) and dicyclohexylcarbodiimide (15 g) in dichloromethane (105 ml) according to J. Org. Chem., 52, 2319 (1987). The reaction mixture is allowed to react at room temperature for 2.5 hours and then filtered and evaporated to dryness in vacuo. The residue is purified over a flash column using toluene/ethyl acetate 10/1 as eluant, yielding 3-ethoxy-1,1'-carbonyldipyrrole-2-carboxylic acid ethyl ester, m.p. 58°–60° C. (3.15 g), which is dissolved in acetic acid (75 ml) and reacted with palladium (II) acetate (1.3 g) under inert atmosphere at 80° C. for 7 hours. After cooling the reaction mixture is filtered and evaporated to dryness in vacuo. The residue is purified over a flash column using toluene/ethyl acetate 10:1 as eluant, yielding 0.87 g of 4-ethoxy-1,1'-carbonyl-2,2'-bipyrrole-5-carboxylic acid ethyl ester, m.p. 100°–103° C., and 1.32 g of recovered starting material.

The obtained bipyrrole is dissolved in methanol (63 ml) and treated with lithium methoxide (3.17 ml of 1N solution in methanol) under stirring at room temperature for 40 minutes. The reaction mixture is diluted with ice water and the precipitate is filtered and thoroughly washed with water until neutral, so obtaining pure 4-ethoxy-2,2'-bipyrrole-5-carboxylic acid ethyl ester, m.p. 189°–191° C. (0.7 g), which is reacted with hydrazine hydrate (20 ml) under stirring at 60° for 8 hours. After cooling the reaction mixture is diluted with ice water and the precipitate is filtered and washed thoroughly with water until neutral to give 4-ethoxy-2,2'-bipyrrole-5-carbohydrazide, m.p. 255°–257° C., (0.63 g), which is reacted with p-toluensulfonyl chloride (0.51 g) in pyridine (18 ml) under stirring at room temperature for 1 hour. The reaction mixture is diluted with ice water and acidified to pH 4 with 37% HCl. The precipitate is filtered and washed with water until neutral to yield 4-ethoxy-2,2'-bipyrrole-5-carbox-p-toluenesulfonhydrazide, m.p. 272°–275° C. (0.97 g), which is dissolved in ethylene glycol (10 ml) at 150° C. and treated under stirring at this temperature with anhydrous sodium carbonate (0.92 g) for 3 minutes. After cooling the reaction mixture is diluted with ice water and the precipitate is extracted with ethyl acetate, washed with water until neutral and evaporated to dryness in vacuo. The residue is purified over a flash column using hexane/ethyl acetate 7:3 as eluent to give 0.28 g of 4-ethoxy-2,2'-bipyrrole-5-carboxaldehyde, m.p. 218°–220° C.. The aldehyde above (0.05 g) is reacted with 2-undecyl-pyrrole (0.065 g) in methanol (40 ml) under stirring in the presence of 10 eq. of gaseous HCl in ether at room temperature for 18 hours.

The reaction mixture is diluted with water (200 ml) and extracted with dichloromethane. The organic phase is shacked with 5% ammonium hydroxide solution and then evaporated to dryness in vacuo. The residue is purified over a short basic $Al_2O_3$ column using ethyl acetate as eluant. The collected fractions are shacked with 1N HCl and then evaporated to dryness in vacuo to give a residue which is crystallized by treatment with pentane, yielding 0.036 g of 4-ethoxy-5-[(5-undecyl-2H-pyrrol-2-ylidene)methyl]-2,2'-bi-1H-pyrrole, hydrochloride, m.p. 94°–96° C., NMR (CDCl$_3$) δ ppm: 0.85 (m) (3H, —(CH$_2$)$_9$—C$H_3$), 1.1–1.9 (m) (21H, —(C$H_2$)$_9$—+OCH$_2$C$H_3$), 2.95 (m) (2H, —C$H_2$—(CH$_2$)$_9$—), 4.25 (q, J=7.0 Hz) (2H, OC$H_2$CH$_3$), 6.05 (d, J=1.8 Hz) (1H, C-3 bipyrrole proton), 6.21 (dd, J=1.5 Hz, J=4.0 Hz) (1H, C-4 pyrrole proton), 6.37 (m) (1H, C-4' bipyrrole proton), 6.86 (dd, J=4.0 Hz, J=2.4 Hz) (1H, C- 3 pyrrole proton), 6.94 (m) (1H, C-3' bipyrrole proton), 7.03 (s) (1H, —CH=), 7.25 (m) (1H, C-5' bipyrrole proton ), 12.6–13 (two bs) (3H, —NH—).

By proceeding analogously the following compounds can be prepared:

4-ethoxy-5-{[5-(undec-10-en-1-yl) -2H-pyrrol-2-ylidene] methyl}-2,2'-bi-1H-pyrrole, hydrochloride, m.p. =80°–97° C.;
4-ethoxy-5-[(5-decyl-2H-pyrrol-2-ylidene) methyl]-2,2'-bi-1H-pyrrole, hydrochloride;
4-ethoxy-5-[(5-dodecyl-2H-pyrrol-2-ylidene)methyl]-2,2'-bi-1H-pyrrole, hydrochloride;
4-ethoxy-5-[(5-phenethyl-2H-pyrrol-2-ylidene)methyl]-2,2'-bi-1H-pyrrole, hydrochloride.
4-ethoxy-5-{[5-(5-phenoxy-pent-1-yl )-2H-pyrrol-2-ylidene]methyl}-2,2'-bi-1H-pyrrole, hydrochloride, m.p. 110°–120° C.;
4-ethoxy-5-[(5-tridecyl-2H-pyrrol-2-ylidene)methyl]-2,2'-bi-1H-pyrrole, hydrochloride, m.p. 88°–93° C.; and
4-ethoxy-5-[(5-methyl-2H-pyrrol-2-ylidene)methyl]-2,2'-bis-1H-pyrrole, hydrochloride, m.p. 200° C.(dec.).

EXAMPLE 2

By proceeding according to Example 1, condensing suitable 4-alkoxy-2,2'-bi-1H-pyrrole-5-carboxaldehydes with suitable substituted pyrroles, the following compounds can be prepared:

4-amyloxy-5-[(5-undecyl-2H-pyrrol-2-ylidene)methyl]-2,2'-bi-1H-pyrrole, hydrochloride;
4-undecyloxy-5-[(5-undecyl-2H-pyrrol-2-ylidene)methyl]-2,2'-bi-1H-pyrrole, hydrochloride;
4-undecyloxy-5-[(2H-pyrrol-2-ylidene)methyl]-2,2'-bi-1H-pyrrole, hydrochloride;
4-buthoxy-5-[(5-tridecyl-2H-pyrrol-2-ylidene)methyl]-2,2'-bi-1H-pyrrole, hydrochloride;
4-benzyloxy-5-[(5-tridecyl-2H-pyrrol-2-ylidene)methyl]-2,2'-bi-1H-pyrrole, hydrochloride;
4-buthoxy-5-[[5-(5-phenoxy-pent-1-yl)-2H-pyrrol-2-ylidene]methyl]-2,2'-bi-1H-pyrrole, hydrochloride;
4-benzyloxy-5-[[5-(5-phenoxy-pent-1-yl)-2H-pyrrol-2-ylidene]methyl]-2,2'-bi-1H-pyrrole, hydrochloride;
4-propoxy-5-[(5-undecyl-2H-pyrrol-2-ylidene)methyl]-2,2'-bi-1H-pyrrole, hydrochloride, m.p. 73°–77° C.;
4-butoxy-5-[(5-undecyl-2H-pyrrol-2-ylidene)methyl]-2,2'-bi-1H-pyrrole, hydrochloride, m.p. 81°–83° C.;
4-isopropoxy-5-[(5-undecyl-2H-pyrrol-2-ylidene)methyl]-2,2'-bi-1H-pyrrole, hydrochloride;
4-propoxy-5-[(5-decyl-2H-pyrrol-2-ylidene)methyl]-2,2'-bi-1H-pyrrole, hydrochloride;
4-propoxy-5-[(5-dodecyl-2H-pyrrol-2-ylidene)methyl]-2,2'-bi-1H-pyrrole, hydrochloride;
4-propoxy-5-{[5-(undec-10-en-1-yl)-2H-pyrrol-2-ylidene] methyl}-2,2'-bi-1H-pyrrole, hydrochloride;
4-propoxy-5-{[5-(5-phenoxy-pent-1-yl)-2H-pyrrol-2-ylidene]methyl}-2,2'-bi-1H-pyrrole, hydrochloride;
4-benzyloxy-5-[(5-undecyl-2H-pyrrol-2-ylidene)methyl]-2,2'-bi-1H-pyrrole, hydrochloride, m.p. 90°–93° C.; and
4-benzyloxy-5-[(2H-pyrrol-2-ylidene)methyl]-2,2'-bi-1H-pyrrole, hydrochloride, m.p. 200°–202° C.

EXAMPLE 3

By proceeding according to Example 1, condensing 4-methoxy-2,2'-bi-1H-pyrrole-5-carboxaldehyde with suitable substituted pyrroles, the following compounds can be prepared:

4-methoxy-5-[[5-(7-cyano-hept-1-yl)-2H-pyrrol-2-ylidene] methyl]-2,2'-bi-1H-pyrrole, hydrochloride;
4-methoxy-5-{[5-(undec-10-en-1-yl)-2H-pyrrol-2-ylidene] methyl}-2,2'-bi-1H-pyrrole, hydrochloride;
4-methoxy-5-[(5-decyl-2H-pyrrol-2-ylidene)methyl]-2,2'-bi-1H-pyrrole, hydrochloride, m.p. 100°–116° C.;
4-methoxy-5-[(5-dodecyl-2H-pyrrol-2-ylidene)methyl]-2,2'-bi-1H-pyrrole, hydrochloride;
4-methoxy-5-[(5-tridecyl-2H-pyrrol-2-ylidene)methyl]-2,2'-bi-1H-pyrrole, hydrochloride, m.p. 80°–100° C.;
4-methoxy-5-[(5-pentadecyl-2H-pyrrol-2-ylidene)methyl]-2,2'-bi-1H-pyrrole, hydrochloride, m.p.=100°–104° C.;
4-methoxy-5-[(5-propyl-2H-pyrrol-2-ylidene)methyl]-2,2'-bi-1H-pyrrole, hydrochloride;
4-methoxy-5-[(5-heptyl-2H-pyrrol-2-ylidene)methyl]-2,2'-bi-1H-pyrrole, hydrochloride, m.p. 140°–145° C.;
4-methoxy-5-[(5-phenethyl-2H-pyrrol-2-ylidene)methyl]-2,2'-bi-1H-pyrrole, hydrochloride, m.p. 170° C. dec.;
4-methoxy-5-[(5-methyl-4-undecyl-2H-pyrrol-2-ylidene) methyl]-2,2'-bi-1H-pyrrole, hydrochloride;
4-methoxy-5-[(5-propyl-4-undecyl-2H-pyrrol-2-ylidene) methyl]-2,2'-bi-1H-pyrrole, hydrochloride;
4-methoxy-5-{[5-(5-phenoxy-pent-1-yl)-2H-pyrrol-2-ylidene]methyl}-2,2'-bi-1H-pyrrole, hydrochloride, m.p. 126°–129° C.;
4-methoxy-5-[(4-ethyl-3,5-dimethyl-2H-pyrrol-2-ylidene) methyl]-2,2'-bi-1H-pyrrole, hydrochloride;
4-methoxy-5-[(4-hexyl-5-methyl-2H-pyrrol-2-ylidene) methyl]-2,2'-bi-1H-pyrrole, hydrochloride;

4-methoxy-5-[(5-nonyl-2H-pyrrol-2-ylidene)methyl]-2,2'-bi-1H-pyrrole, hydrochloride;

4-methoxy-5-[(5-methyl-4-pentyl-2H-pyrrol-2-ylidene) methyl]-2,2'-bi-1H-pyrrole, hydrochloride;

4-methoxy-5-{[5-(5-carboxy-pent-1-yl)-2H-pyrrol-2-ylidene]methyl}-2,2'-bi-1H-pyrrole, hydrochloride, m.p. 57°–165° C.;

4-methoxy-5-{[5-(5-carboxy-pent-1-yl)-2H-pyrrol-2-ylidene]methyl}-2,2'-bi-1H-pyrrole, methyl ester, hydrochloride, m.p. 138°–140° C.;

4-methoxy-5-{[5-(6-hydoxy-hex-1-yl)-2H-pyrrol-2-ylidene]methyl}-2,2'-bi-1H-pyrrole, hydrochloride, m.p. 18°–121° C.;

4-methoxy-5-{[5-(6-fluoro-hex-1-yl)-2H-pyrrol-2-ylidene] methyl}-2,2'-bi-1H-pyrrole, hydrochloride, m.p. 115°–124° C.; and 4-methoxy-5-{[5-(5-morpholinecarboxamido-pent-1-yl)-2H-pyrrol-2-ylidene]methyl}-2,2'-bi-1H-pyrrole, hydrochloride.

EXAMPLE 4

By proceeding according to Examples 1 and 2, using suitable substituted pyrroles, the following compounds can be prepared:

4-ethoxy-5-[(5-ethyl-4-pentyl-2H-pyrrol-2-ylidene) methyl]-2,2'-bi-1H-pyrrole, hydrochloride;

4-ethoxy-5-[(5-methyl-4-pentyl-2H-pyrrol-2-ylidene) methyl]-2,2'-bi-1H-pyrrole, hydrochloride;

4-ethoxy-5-[(5-ethyl-4-undecyl-2H-pyrrol-2-ylidene) methyl]-2,2'-bi-1H-pyrrole, hydrochloride;

4-ethoxy-5-[(5-methyl-4-undecyl-2H-pyrrol-2-ylidene) methyl]-2,2'-bi-1H-pyrrole, hydrochloride;

4-ethoxy-5-[(5-heptyl-4-undecyl-2H-pyrrol-2-ylidene) methyl]-2,2'-bi-1H-pyrrole, hydrochloride;

4-propoxy-5-[(5-ethyl-4-undecyl-2H-pyrrol-2-ylidene) methyl]-2,2'-bi-1H-pyrrole, hydrochloride;

4-ethoxy-5-[(4-ethyl-3,5-dimethyl-2H-pyrrol-2-ylidene) methyl]-2,2'-bi-1H-pyrrole, hydrochloride;

4-ethoxy-5-{[5-(5-carboxy-pent-1-yl)-2H-pyrrol-2-ylidene] methyl}-2,2'-bi-1H-pyrrole;

4-propoxy-5-{[5-(5-carboxy-pent-1-yl)-2H-pyrrol-2-ylidene]methyl}-2,2'-bi-1H-pyrrole;

4-ethoxy-5-{[5-(6-hydroxy-hex-1-yl)-2H-pyrrol-2-ylidene] methyl}-2,2'-bi-1H-pyrrole;

4-propoxy-5-{[5-(6-hydroxy-hex-1-yl)-2H-pyrrol-2-ylidene]methyl}-2,2'-bi-1H-pyrrole;

4-propoxy-5-{[5-(11-carboxy-undec-1-yl)-2H-pyrrol-2-ylidene]methyl}-2,2'-bi-1H-pyrrole;

4-propoxy-5-{[5-(12-carboxy-dodec-1-yl)-2H-pyrrol-2-ylidene]methyl}-2,2'-bi-1H-pyrrole;

4-propoxy-5-{[5-(12-hydroxy-dodec-1-yl)-2H-pyrrol-2-ylidene]methyl}-2,2'-bi-1H-pyrrole, hydrochloride;

4-propoxy-5-{[5-(13-hydroxy-tridec-1-yl)-2H-pyrrol-2-ylidene]methyl}-2,2'-bi-1H-pyrrole, hydrochloride;

4-propoxy-5-{[5-(11-cyano-undec-1-yl)-2H-pyrrol-2-ylidene]methyl}-2,2'-bi-1H-pyrrole, hydrochloride;

4-propoxy-5-{[5-(11-carbamoyl-undec-1-yl)-2H-pyrrol-2-ylidene]methyl}-2,2'-bi-1H-pyrrole, hydrochloride;

4-propoxy-5-{[5-(11-ethoxycarbonyl-undec-1-yl)-2H-pyrrol-2-ylidene]methyl}-2,2'-bi-1H-pyrrole, hydrochloride.

4-ethoxy-5-[(5-undecanoyl-2H-pyrrol-2-ylidene)methyl]-2,2'-bi-1H-pyrrole, hydrochloride;

4-ethoxy-5-{[5-(11-carboxy-undec-1-yl)-2H-pyrrol-2-ylidene]methyl}-2,2'-bi-1H-pyrrole;

4-ethoxy-5-{[5-(12-carboxy-dodec-1-yl)-2H-pyrrol-2-ylidene]methyl}-2,2'-bi-1H-pyrrole;

4-ethoxy-5-{[5-(12-hydroxy-dodec-1-yl)-2H-pyrrol-2-ylidene]methyl}-2,2'-bi-1H-pyrrole, hydrochloride;

4-ethoxy-5-{[5-(13-hydroxy-tridec-1-yl)-2H-pyrrol-2-ylidene]methyl}-2,2'-bi-1H-pyrrole, hydrochloride;

4-ethoxy-5-{[5-(11-cyano-undec-1-yl)-2H-pyrrol-2-ylidene]methyl}-2,2'-bi-1H-pyrrole, hydrochloride;

4-ethoxy-5-{[5-(11-carbamoyl-undec-1-yl)-2H-pyrrol-2-ylidene]methyl}-2,2'-bi-1H-pyrrole, hydrochloride; and 4-ethoxy-5-{[5-(11-ethoxycarbonyl-undec-1-yl)-2H-pyrrol-2-ylidene]methyl}-2,2'-bi-1H-pyrrole, hydrochloride.

EXAMPLE 5

By proceeding according to Examples 1–3, condensing a suitable 4-alkoxy-2,2'-bi-1H-pyrrole-5-carboxaldehyde with pyrroles carrying suitable cyclic substituents, the following compounds can be prepared:

4-methoxy-5-[(4,5,6,7-tetrahydro-2H-indol-2-ylidene) methyl]-2,2'-bi-1H-pyrrole, hydrochloride, m.p. 212° C. dec.;

4-methoxy-5-[(4-hexyl-4,5,6,7-tetrahydro-2H-indol-2-ylidene)methyl]-2,2'-bi-1H-pyrrole, hydrochloride, m.p. 181°–184° C.;

4-ethoxy-5-[(4-hexyl-4,5,6,7-tetrahydro-2H-indol-2-ylidene)methyl]-2,2'-bi-1H-pyrrole, hydrochloride;

4-propoxy-5-[(4-hexyl-4,5,6,7-tetrahydro-2H-indol-2-ylidene)methyl]-2,2'-bi-1H-pyrrole, hydrochloride;

4-ethoxy-5-{[4-(4-carboxy-but-1-yl)-4,5,6,7-tetrahydro-2H-indol-2-ylidene]methyl}-2,2'-bi-1H-pyrrole;

4-ethoxy-5-[(3,5-nonamethylene-2H-pyrrol-2-ylidene) methyl]-2,2'-bi-1H-pyrrole, hydrochloride;

4-propoxy-5-[(3,5-nonamethylene-2H-pyrrol-2-ylidene) methyl]-2,2'-bi-1H-pyrrole, hydrochloride; and 4-ethoxy-5-{[4-(4-ethoxycarbonyl-but-1-yl)-4,5,6,7-tetrahydro-2H-indol-2-ylidene]methyl}-2,2'-bi-1H-pyrrole, hydrochloride.

EXAMPLE 6

By proceeding according to Examples 1–5, condensing a suitable 5'-substituted-4-alkoxy-2,2'-bi-1H-pyrrole-5-carboxaldehyde, prepared starting from a suitable 5-substituted pyrrole-1-carboxylic acid, with suitable substituted pyrroles, the following compounds can be prepared:

4-ethoxy-5'-methyl-5-[(5-methyl-2H-pyrrol-2-ylidene) methyl]-methyl]-2,2'-bi-1H-pyrrole, hydrochloride, m.p. 180° C. (dec);

4-propoxy-5'-methyl-5-[(5-undecyl-2H-pyrrol-2-ylidene) methyl]-2,2'-bi-1H-pyrrole, hydrochloride;

4-ethoxy-5'-methyl-5-{[5-(undec-10-en-1-yl)-2H-pyrrol-2-ylidene]methyl}-2,2'-bi-1H-pyrrole, hydrochloride;

4-ethoxy-5'-methyl-5-[(5-decyl-2H-pyrrol-2-ylidene) methyl]-2,2'-bi-1H-pyrrole, hydrochloride;

4-ethoxy-5'-methyl-5-[(5-dodecyl-2H-pyrrol-2-ylidene) methyl]-2,2'-bi-1H-pyrrole, hydrochloride;

4-ethoxy-5'-methyl-5-[(3,5-nonamethylene-2H-pyrrol-2-ylidene)methyl]-2,2'-bi-1H-pyrrole, hydrochloride;

4-ethoxy-5'-heptyl-5-[(5-undecyl-2H-pyrrol-2-ylidene) methyl]-2,2'-bi-1H-pyrrole, hydrochloride; and 4-ethoxy-5'-methyl-5-[(5-undecyl-2H-pyrrol-2-ylidene) methyl]-2,2'-bi-1H-pyrrole, hydrochloride.

EXAMPLE 7

By proceeding according to Examples 1–6, condensing a suitable 3-cyano-4-alkoxy-2,2'-bi-1H-pyrrole-5-carboxaldehyde, prepared starting from a suitable 4-cyano- 3-hydroxy-pyrrole-2-carboxylic acid alkyl ester, with suitable substituted pyrroles, the following compounds can be prepared:

3-cyano-4-propoxy-5-[(5-undecyl-2H-pyrrol-2-ylidene)methyl]-2,2'-bi-1H-pyrrole, hydrochloride;
3-cyano-4-ethoxy-5-[(5-undecyl-2H-pyrrol-2-ylidene)methyl]-2,2'-bi-1H-pyrrole, hydrochloride;
3-cyano-4-ethoxy-5-{[5-(undec-10-en-1-yl)-2H-pyrrol-2-ylidene]methyl}-2,2'-bi-1H-pyrrole, hydrochloride; and
3-cyano-4-ethoxy-5'-methyl-5-[(5-undecyl-2H-pyrrol-2-ylidene)methyl]-2,2'-bi-1H-pyrrole, hydrochloride.

EXAMPLE 8

By reacting, according to the method described in the Example 1, suitable substituted 2-formyl-pyrroles with suitable 5'-substituted 3-alkoxycarbonyl-4-alkoxy-2,2'-bi-1H-pyrroles, prepared by condensation of suitable 3-alkoxycarbonyl-4-alkoxy-3-pyrrolin-2-ones of formula (VIII) with suitable 2-substituted pyrroles of formula (IX) the following compounds can be prepared:

3-ethoxycarbonyl-4-propoxy-5'-methyl-5-[(5-undecyl-2H-pyrrol-2-ylidene)methyl]-2,2'-bi-1H-pyrrole, hydrochloride;
3-ethoxycarbonyl-4-ethoxy-5'-methyl-5-[(5-undecyl-2H-pyrrol-2-ylidene)methyl]-2,2'-bi-1H-pyrrole, hydrochloride;
3-ethoxycarbonyl-4-ethoxy-5'-methyl-5-{[5-undec-10-en-1-yl)-2H-pyrrol-2-ylidene])methyl}-2,2'-bi-1H-pyrrole, hydrochloride;
3-methoxycarbonyl-4-methoxy-5'-methyl-5-[(5-undecyl-2H-pyrrol-2-ylidene)methyl]-2,2'-bi-1H-pyrrole, hydrochloride;
3-ethoxycarbonyl-4-ethoxy-5'-methyl-5-[(3,5-nonamethylene-2H-pyrrol-2-ylidene)methyl]-2,2'-bi-1H-pyrrole, hydrochloride;
3-ethoxycarbonyl-4-ethoxy-5'-propyl-5-[(5-undecyl-2H-pyrrol-2-ylidene)methyl]-2,2'-bi-1H-pyrrole, hydrochloride; and 3-ethoxycarbonyl-4-propoxy-5'-methyl-5-{[5-(undec-10-en-1-yl)-2H-pyrrol-2-ylidene]methyl}-2,2'-bi-1H-pyrrole, hydrochloride.

EXAMPLE 9

By proceeding according to Example 8 and condensing suitable substituted 2-formyl-pyrroles with suitable 5'-substituted 3-carboxy-4-alkoxy-2,2'-bi-1H-pyrroles, the following compounds can be prepared:

3-carboxy-4-propoxy-5'-methyl-5-[(5-undecyl-2H-pyrrol-2-ylidene)methyl]-2,2'-bi-1H-pyrrole;
3-carboxy-4-ethoxy-5'-methyl-5-[(5-undecyl-2H-pyrrol-2-ylidene)methyl]-2,2'-bi-1H-pyrrole;
3-carboxy-4-ethoxy-5'-methyl-5-{[5-(undec-10-en-1-yl)-2H-pyrrol-2-ylidene]methyl}-2,2'-bi-1H-pyrrole; and
3-carboxy-4-ethoxy-5'-propyl-5-[(5-undecyl-2H-pyrrol-2-ylidene)methyl]-2,2'-bi-1H-pyrrole.

EXAMPLE 10

Formulation: capsules (150 mg).

Capsules, each weighing 400 mg and containing 150 mg of the active substance, are manufactured as follows:

Composition:

| | |
|---|---|
| 4-ethoxy-5-[(5-undecyl-2H-pyrrol-2-ylidene)methyl]-2,2'-bi-1H-pyrrole, hydrochloride | 150 mg |
| Lactose | 198 mg |
| Corn starch | 50 mg |
| Magnesium stearate | 2 mg |
| Total | 400 mg |

Encapsulate in two-piece hard gelatin capsules.

We claim:
1. A 5-[2H-pyrrol-2-ylidene)methyl]-2,2'-bi-1H-pyrrole compound having the following formula (I)

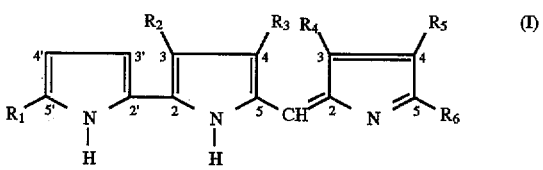

wherein $R_1$ represents hydrogen, phenyl, $C_1$–$C_{20}$ alkyl or $C_2$–$C_{20}$ alkenyl, wherein the alkyl and alkenyl groups are unsubstituted or substituted by 1 to 3 substituents chosen independently from halogen, $C_1$–$C_6$ alkoxy, hydroxy, aryl and aryloxy;

$R_2$ represents hydrogen, $C_1$–$C_6$ alkyl, cyano, carboxy or ($C_1$–$C_6$ alkoxy)carbonyl;

$R_3$ represents halogen, hydroxy or $C_1$–$C_{11}$ alkoxy unsubstituted or substituted by phenyl;

$R_4$ represents hydrogen, $C_1$–$C_6$ alkyl or phenyl;

each of $R_5$ and $R_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups are unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkyl-carbamoyl, arylcarbamoyl and —$CONR_cR_d$ in which each of $R_c$ and $R_d$ independently is hydrogen or $C_1$–$C_6$ alkyl or $R_c$ and $R_d$, taken together with the nitrogen atom to which they are linked, form a morpholino or piperidino ring;

or two of $R_4$, $R_5$ and $R_6$ taken together form a $C_4$–$C_{12}$ polymethylene chain, which is unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups are in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl;

or a pharmaceutically acceptable salt thereof; and wherein when at the same time $R_3$ is methoxy and $R_1$, $R_2$, $R_4$ and $R_5$ are hydrogen, then $R_6$ is other than hydrogen, n-nonyl or n-undecyl; and wherein when at the same time $R_3$ is methoxy and $R_1$, $R_2$, $R_4$ and $R_6$ are hydrogen, then $R_5$ is other than n-undecyl; and wherein when at the same time $R_3$ is methoxy, and $R_1$ and $R_2$ are hydrogen, and $R_4$ and $R_6$ are methyl, then $R_5$ is other than hydrogen or ethyl; and wherein when at the same time $R_3$ is methoxy and $R_1$, $R_2$ and $R_5$, are hydrogen, then $R_4$ and $R_6$, taken together, are other than an α-ethyl-nonamethylene or α-butyl-heptamethylene chain; and wherein when at the same time $R_3$ is methoxy, $R_6$ is methyl and $R_1$, $R_2$ and $R_4$ are hydrogen, then $R_5$ is other than n-pentyl, n-hexyl, n-heptyl or n-undecyl; and wherein when at the same time $R_3$ is methoxy and $R_1$, $R_2$ and $R_4$ are hydrogen, then $R_5$ and $R_6$, taken together, are other than α-butyl-heptamethylene chain; or $R_5$ being methyl, then $R_6$ is other than n-pentyl; or $R_5$ being ethyl, then $R_6$ is other than n-butyl; and wherein when at the same time $R_3$ is hydroxy, $R_1$, $R_2$ and $R_4$ are hydrogen and $R_6$ is methyl, then $R_5$ is other than n-pentyl; and wherein when at the same time $R_3$ is methoxy, $R_1$ and $R_2$ are hydrogen and $R_6$ is methyl, then $R_4$ and $R_5$, taken together, are other than an α-methyl-tetra-methylene or β-methyl-tetramethylene chain; or $R_4$ being n-propyl, then $R_5$ is other than n-heptyl.

2. A compound of formula (I), according to claim 1, wherein $R_1$ represents hydrogen, $C_1$–$C_{12}$ alkyl or $C_2$–$C_{12}$ alkenyl, wherein the alkyl and the alkenyl groups are unsubstituted or substituted by aryl or aryloxy;

$R_2$ represents hydrogen, cyano, carboxy or ($C_1$–$C_4$ alkoxy)carbonyl;

$R_3$ represents hydroxy or $C_1$–$C_{11}$ alkoxy unsubstituted or substituted by phenyl;

$R_4$ represents hydrogen or $C_1$–$C_4$ alkyl;

each of $R_5$ and $R_6$ independently represents hydrogen, $C_3$–$C_{14}$ alkyl or $C_3$–$C_{14}$ alkenyl, wherein the alkyl and the alkenyl groups are unsubstituted or substituted by a substituent chosen from halogen, $C_1$–$C_4$ alkoxy, hydroxy, aryl, aryloxy, cyano, carboxy, ($C_1$–$C_4$ alkoxy)carbonyl, aralkylcarbamoyl, arylcarbamoyl and —$CONR_cR_d$ in which each of $R_c$ and $R_d$ independently is hydrogen or $C_1$–$C_4$ alkyl or $R_c$ and $R_d$, taken together with the nitrogen atom to which they are linked, form a morpholino or piperidino ring;

or two of $R_4$, $R_5$ and $R_6$ taken together form a $C_4$–$C_9$ polymethylene chain, which is unsubstituted or substituted by a $C_1$–$C_6$ alkyl, by a $C_3$–$C_6$ alkenyl or by a $C_1$–$C_8$ alkylidene group, wherein the alkyl, alkenyl and alkylidene groups are in turn unsubstituted or substituted by a substituent chosen from halogen, $C_1$–$C_4$ alkoxy, hydroxy, cyano, carboxy, ($C_1$–$C_4$ alkoxy)carbonyl, aryloxy and aryl; the remaining one being hydrogen of $C_1$–$C_6$ alkyl; or a pharmaceutically acceptable salt thereof.

3. A compound selected from:

4-methoxy-5-{[5-(undec-10-en-1-yl)-2H-pyrrol-2-ylidene]methyl}-2,2'-bi-1H-pyrrole;
4-ethoxy-5-[(5-decyl-2H-pyrrol-2-ylidene)methyl]-2,2'-bi-1H-pyrrole;
4-ethoxy-5-[(5-dodecyl-2H-pyrrol-2-ylidene)methyl]-2,2'-bi-1H-pyrrole;
4-ethoxy-5-[(3,5-nonamethylene-2H-pyrrol-2-ylidene)methyl]-2,2'-bi-1H-pyrrole;
4-ethoxy-5-[(5-undecyl-2H-pyrrol-2-ylidene)methyl]-2,2'-bi-1H-pyrrole;
4-propoxy-5-[(5-undecyl-2H-pyrrol-2-ylidene)methyl]-2,2'-bi-1H-pyrrole;
4-ethoxy-5-{[5-(undec-10-en-1-yl)-2H-pyrrol-2-ylidene]methyl}-2,2'-bi-1H-pyrrole;
4-isopropoxy-5-[(5-undecyl-2H-pyrrol-2-ylidene) methyl]-2,2'-bi-1H-pyrrole;
4-amyloxy-5-[(5-undecyl-2H-pyrrol-2-ylidene) methyl]-2,2'-bi-1H-pyrrole;
4-undecyloxy-5-[(5-undecyl-2H-pyrrol-2-ylidene) methyl]-2,2'-bi-1H-pyrrole;
4-benzyloxy-5-[(5-undecyl-2H-pyrrol-2-ylidene) methyl]-2,2'-bi-1H-pyrrole;
4-benzyloxy-5-[(2H-pyrrol-2-ylidene)methyl]-2,2'-bi-1H-pyrrole;
4-undecyloxy-5-[(2H-pyrrol-2-ylidene)methyl]-2,2'-bi-1H-pyrrole;
4-methoxy-5-[(5-tridecyl-2H-pyrrol-2-ylidene) methyl]-2,2'-bi-1H-pyrrole;
4-ethoxy-5-[(5-tridecyl-2H-pyrrol-2-ylidene) methyl]-2,2'-bi-1H-pyrrole;
4-butoxy-5-[(5-tridecyl-2H-pyrrol-2-ylidene) methyl]-2,2'-bi-1H-pyrrole;
4-benzyloxy-5-[(5-tridecyl-2H-pyrrol-2-ylidene) methyl]-2,2'-bi-1H-pyrrole;
4-methoxy-5-[[5-(5-phenoxy-pent-1-yl)-2H-pyrrol-2-ylidene]methyl]-2,2'-bi-1H-pyrrole;
4-ethoxy-5-[[5-(5-phenoxy-pent-1-yl)-2H-pyrrol-2-ylidene]methyl]-2,2'-bi-1H-pyrrole;
4-butoxy-5-[[5-(5-phenoxy-pent-1-yl)-2H-pyrrol-2-ylidene]methyl]-2,2'-bi-1H-pyrrole;
4-benzyloxy-5-[[5-(5-phenoxy-pent-1-yl)-2H-pyrrol-2-ylidene]methyl]-2,2'-bi-1H-pyrrole;
4-methoxy-5-[[5-(6-fluoro-hex-1-yl)-2H-pyrrol-2-ylidene]methyl]-2,2'-bi-1H-pyrrole;
4-methoxy-5-[[5-(6-hydoxy-hex-1-yl)-2H-pyrrol-2-ylidene]methyl]-2,2'-bi-1H-pyrrole;
4-methoxy-5-[[5-(5-morpholinecarboxamido-pent-1-yl)-2H-pyrrol-2-ylidene]methyl]-2,2'-bi-1H-pyrrole; and
4-methoxy-5-[[5-(7-cyano-hept-1-yl)-2H-pyrrol-2-ylidene]methyl]-2,2'-bi-1H-pyrrole;

and the pharmaceutically acceptable salts thereof.

4. A salt of a compound, according to claim 3, wherein said salt is a hydrochloride, hydrobromide or methanesulfonate.

5. A pharmaceutical composition comprising a pharmaceutically acceptable carrier and/or diluent and as an active principle a compound of formula (I) as defined in claim 1, or a salt thereof.

6. A process for the preparation of a compound of formula (I) or a salt thereof, the process comprising:

A) reacting a compound of formula (II)

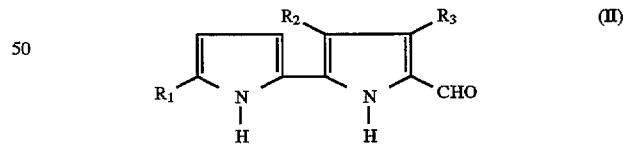

wherein $R_1$, $R_2$ and $R_3$ are as defined in claim 1, with a compound of formula (III)

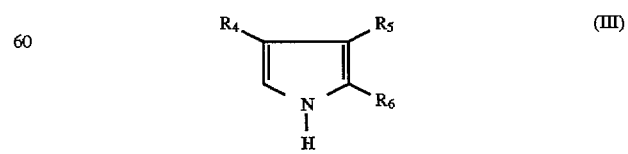

wherein $R_4$, $R_5$ and $R_6$ are as defined in claim 1; or

B) reacting a compound of formula (IV)

$$\text{(IV)}$$

wherein $R_a$ is as $R_1$ defined in claim 1 except hydrogen and $R_2$ and $R_3$ are as defined in claim 1, with a compound of formula (V)

$$\text{(V)}$$

wherein $R_4$, $R_5$ and $R_6$ are as defined in claim 1 so obtaining a compound of formula (I) as defined in claim 1 wherein $R_1$ is other than hydrogen.

7. A parmaceutical composition comprising a pharmaceutically acceptable carrier and/or diluent and as an active principle a compound of formula (IB)

$$\text{(IB)}$$

wherein $R'_1$ represents hydrogen, phenyl, $C_1$–$C_{20}$ alkyl or $C_2$–$C_{20}$ alkenyl, wherein the alkyl and alkenyl groups are unsubstituted or substituted by 1 to 3 substituents chosen independently from halogen, $C_1$–$C_6$ alkoxy, hydroxy, aryl and aryloxy;

$R'_2$ represents hydrogen, $C_1$–$C_6$ alkyl, cyano, carboxy or ($C_1$–$C_6$ alkoxy)carbonyl;

$R'_3$ represents halogen, hydroxy or ($C_1$–$C_{11}$ alkoxy unsubstituted or substituted by phenyl;

$R'_4$ represents hydrogen, $C_1$–$C_6$ alkyl or phenyl;

each of $R'_5$ and $R'_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups are unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralklcarbamoyl, arylcarbamoyl and —$CONR_cR_d$ in which each of $R_c$ and $R_d$ independently is hydrogen or $C_1$–$C_6$ alkyl or $R_c$ and $R_d$, taken together with the nitrogen atom to which they are linked, form a morpholino or piperidino ring; or two of $R'_4$, $R'_5$ and $R'_6$ taken together form a $C_4$–$C_{12}$ polymethylene chain, which is unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups are in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl; or a pharmaceutically acceptable salt thereof; and wherein when at the same time $R'_3$ is methoxy and $R'_1$, $R'_2$, $R'_4$ and $R'_5$ are hydrogen, then $R'_6$ is other than n-nonyl or n-undecyl; and wherein when at the same time $R'_3$ is methoxy and $R'_1$, $R'_2$ and $R'_5$ are hydrogen, then $R'_4$ and $R'_6$, taken together, are other than an α-ethyl-nonamethylene chain; and wherein when it the same time $R'_3$ is methoxy, $R'_6$ is methyl and $R'_1$, $R'_2$ and $R'_4$ are hydrogen, then $R'_5$ is other than n-pentyl; and wherein when at the same time $R'_3$ is methoxy and $R'_1$, $R'_2$ and $R'_4$ are hydrogen, then $R'_5$ and $R'_6$, taken together, are other than an α-butyl-heptamethylene chain; and wherein when at the same time $R'_3$ is hydroxy, $R'_1$, $R'_2$ and $R'_4$ are hydrogen and $R'_6$ is methyl, then $R'_5$ is other than n-pentyl; and wherein when at the same time $R'_3$ is methoxy, $R'_1$ and $R'_2$ are hydrogen and $R'_6$ is methyl, then $R'_4$ and $R'_5$, taken together, are other than an α-methyltetramethylene chain, or a pharmaceutically acceptable salt thereof.

8. A method of treating a mammal in need of an immunomodulating agent, said method comprising administering to said mammal an effective amount of a compound of formula (IC)

$$\text{(IC)}$$

wherein $R''_1$ represents hydrogen, phenyl, $C_1$–$C_{20}$ alkyl or $C_2$–$C_{20}$ alkenyl, wherein the alkyl and alkenyl groups are unsubstituted or substituted by 1 to 3 substituents chosen independently from halogen, $C_1$–$C_6$ alkoxy, hydroxy, aryl and aryloxy;

$R''_2$ represents hydrogen, $C_1$–$C_6$ alkyl, cyano, carboxy or ($C_1$–$C_6$ alkoxy)carbonyl;

$R''_3$ represents halogen, hydroxy or $C_1$–$C_{11}$ alkoxy unsubstituted or substituted by phenyl;

$R''_4$ represents hydrogen, $C_1$–$C_6$ alkyl or phenyl;

each of $R''_5$ and $R''_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups are unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkyl-carbamoyl, arylcarbamoyl and —$CONR_cR_d$ in which each of $R_c$ and $R_d$ independently is hydrogen or $C_1$–$C_6$ alkyl or $R_c$ and $R_d$, taken together with the nitrogen atom to which they are linked, form a morpholino or piperidino ring; or two of $R''_4$, $R''_5$ and $R''_6$ taken together form a $C_4$–$C_{12}$ polymethylene chain, which is unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups are in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl; or a pharmaceutically acceptable salt thereof; and wherein when at the same time $R''_3$ is methoxy and $R''_1$, $R''_2$, $R''_4$ and $R''_5$ are hydrogen, then $R''_6$ is other than n-undecyl; and wherein when at the same time R"₃ is methoxy and R"₁, R"₂ and R"₅ are hydrogen, then R"₄ and R"₆, taken together, are other than an α-ethyl-nonamethylene chain; and wherein when at the same time R"₃ is methoxy and R"₁, R"₂ and R"₄ are hydrogen, then R"₅ and R"₆, taken together, are other than an α-butyl-heptamethylene chain.

9. The method according to claim 8, wherein in the compound of formula (IC),

R"₁ represents hydrogen, C₁–C₂ alkyl or C₂–C₁₂ alkenyl, wherein the alkyl and alkenyl groups are unsubstituted or substituted by aryl or aryloxy;

R"₂ represents hydrogen, cyano, carboxy or (C₁–C₄ alkoxy)carbonyl;

R"₃ represents halogen, hydroxy or C₁–C₄ alkoxy unsubstituted or substituted by phenyl;

R"₄ represents hydrogen or C₁–C₄ alkyl;

each or R"₅ and R"₆ independently represents hydrogen, C₃–C₁₄ alkyl or C₃–C₁₄ alkenyl, wherein the alkyl and the alkenyl groups are unsubstituted or substituted by a substituent chosen from halogen, C₁–C₄ alkoxy, hydroxy, aryl, aryloxy, cyano, carboxy, (C₁–C₄ alkoxy) carbonyl aralkylcarbamoyl, arylcarbamoyl and —CONR_cR_d in which each of R_c and R_d independently is hydrogen or C₁–C₄ alkyl or R_c and R_d, taken together form a morpholino or piperidino ring; or two of R"₄, R"₅ and R"₆ taken together form a C₄–C₉ polymethylene chain, which is unsubstituted or substituted by a C₁–C₆ alkyl, by a C₃–C₆ alkenyl or by a C₁–C₈ alkylidene group, wherein the alkyl, alkenyl and alkylidene groups are in turn unsubstituted or substituted by a substituent chosen from halogen, C₁–C₄ alkoxy, hydroxy, cyano, carboxy, (C₁–C₄ alkoxy) carbonyl, aryloxy and aryl; the remaining one being hydrogen or C₁–C₆ alkyl.

10. The method according to claim 8, wherein the compound of formula (IC) is selected from:

4-methoxy-5-{[5-(undec-10-en-1-yl)-2H-pyrrol-2-ylidene]methyl}-2,2'-bi-1H-pyrrole;
4-ethoxy-5-[(5-decyl-2H-pyrrol-2-ylidene)methyl]-2,2'-bi-1H-pyrrole;
4-ethoxy-5-[(5-dodecyl-2H-pyrrol-2-ylidene)methyl]-2,2'-bi-1H-pyrrole;
4-ethoxy-5-[(3,5-nonamethylene-2H-pyrrol-2-ylidene) methyl]-2,2'-bi-1H-pyrrole;
4-ethoxy-5-[(5-undecyl-2H-pyrrol-2-ylidene)methyl]-2,2'-bi-1H-pyrrole;
4-propoxy-5-[(5-undecyl-2H-pyrrol-2-ylidene) methyl]-2,2'-bi-1H-pyrrole;
4-ethoxy-5-{[5-(undec-10-en-1-yl)-2H-pyrrol-2-ylidene]methyl}-2,2'-bi-1H-pyrrole;
4-methoxy-5-[(4-ethyl-3,5-dimethyl-2H-pyrrol-2-ylidene) methyl]-2,2'-bi-1H-pyrrole;
4-methoxy-5-[(4-hexyl-5-methyl-2H-pyrrol-2-ylidene) methyl]-2,2'-bi-1H-pyrrole;
4-methoxy-5-[(5-methyl-4-undecyl-2H-pyrrol-2-ylidene) methyl]-2,2'-bi-1H-pyrrole;
4-methoxy-5-[(5-nonyl-2H-pyrrol-2-ylidene)methyl]-2,2'-bi-1H-pyrrole;
4-methoxy-5-[(5-methyl-4-pentyl-2H-pyrrol-2-ylidene) methyl]-2,2'-bi-1H-pyrrole;
4-isopropoxy-5-[(5-undecyl-2H-pyrrol-2-ylidene)methyl]-2,2'-bi-1H-pyrrole;
4-amyloxy-5-[(5-undecyl-2H-pyrrol-2-ylidene)methyl]-2,2'-bi-1H-pyrrole;
4-undecyloxy-5-[(5-undecyl-2H-pyrrol-2-ylidene)methyl]-2,2'-bi-1H-pyrrole;
4-benzyloxy-5-[(5-undecyl-2H-pyrrol-2-ylidene)methyl]-2,2'-bi-1H-pyrrole;
4-benzyloxy-5-[(2H-pyrrol-2-ylidene)methyl]-2,2'-bi-1H-pyrrole;
4-undecyloxy-5-[(2H-pyrrol-2-ylidene)methyl]-2,2'-bi-1H-pyrrole;
4-methoxy-5-[(5-tridecyl-2H-pyrrol-2-ylidene)methyl]-2,2'-bi-1H-pyrrole;
4-ethoxy-5-[(5-tridecyl-2H-pyrrol-2-ylidene)methyl]-2,2'-bi-1H-pyrrole;
4-butoxy-5-[(5-tridecyl-2H-pyrrol-2-ylidene)methyl]-2,2'-bi-1H-pyrrole;
4-benzyloxy-5-[(5-tridecyl-2H-pyrrol-2-ylidene)methyl]-2,2'-bi-1H-pyrrole;
4-methoxy-5-[[5-(5-phenoxy-pent-1-yl)-2H-pyrrol-2-ylidene]methyl]-2,2'-bi-1H-pyrrole;
4-ethoxy-5-[[5-(5-phenoxy-pent-1-yl)-2H-pyrrol-2-ylidene] methyl]-2,2'-bi-1H-pyrrole;
4-butoxy-5-[[5-(5-phenoxy-pent-1-yl)-2H-pyrrol-2-ylidene] methyl]-2,2'-bi-1H-pyrrole;
4-benzyloxy-5-[[5-(5-phenoxy-pent-1-yl)-2H-pyrrol-2-ylidene]methyl]-2,2'-bi-1H-pyrrole;
4-methoxy-5-[[5-(6-fluoro-hex-1-yl)-2H-pyrrol-2-ylidene] methyl]-2,2'-bi-1H-pyrrole;
4-methoxy-5-[[5-(6-hydoxy-hex-1-yl)-2H-pyrrol-2-ylidene] methyl]-2,2'-bi-1H-pyrrole;
4-methoxy-5-[[5-(5-morpholinecarboxamido-pent-1-yl)-2H-pyrrol-2-ylidene]methyl]-2,2'-bi-1H-pyrrole; and
4-methoxy-5-[[5-(7-cyano-hept-1-yl)-2H-pyrrol-2-ylidene] methyl]-2,2'-bi-1H-pyrrole;

or a pharmaceutically acceptable salt thereof.

11. A compound of formula (IV)

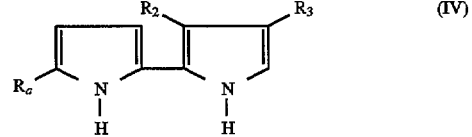

wherein R₂ and R₃ are as defined in claim 1 and R_a is as defined in claim 6.

12. A process for the preparation of a compound of formula (IV) as defined in claim 11, said process comprising C) hydrolysis and decarboxylation of a compound of formula (VII)

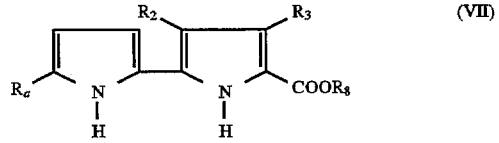

wherein R_a is as defined in claim 6, R₂ and R₃ are as defined in claim 1 and R₈ is C₁–C₆ alkyl; or D) condensation of a compound of formula (VIII)

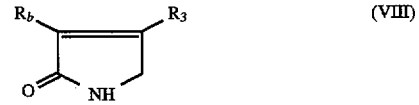

wherein

R₃ is as defined in claim 1 and R_b is as R₂ defined in claim 1 except carboxy, with a compound of formula (IX)

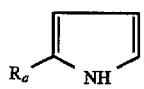

wherein $R_a$ is as defined in claim 6, so obtaining a compound of formula (IV) as defined in claim 11 wherein $R_2$ is other than carboxy.

13. A method for treating in mammals rejection phenomena associated with tissue or organ transplantation, said method comprising administering to said host an effective amount of a compound of formula (IC) as defined in claim 8 or a pharmaceutically acceptable salt thereof.

14. A method for treating in mammals graft-versus-host diseases, said method comprising administering to said host an effective amount of a compound of formula (IC) as defined in claim 8 or a pharmaceutically acceptable salt thereof.

15. A method for treating in mammals autoimmune diseases, said method comprising administering to said host an effective amount of a compound of formula (IC) as defined in claim 8 or a pharmaceutically acceptable salt thereof.

16. A composition comprising a compound of formula (IC), as defined in claim 8, or a pharmaceutically acceptable salt thereof, and an additional compound as a combined preparation for simultaneous, separate or sequential use in immunosuppressant therapy.

17. A 5-[2H-pyrrol-2-ylidene)methyl]-2,2'-bi-1H-pyrrole compound having the following formula (I)

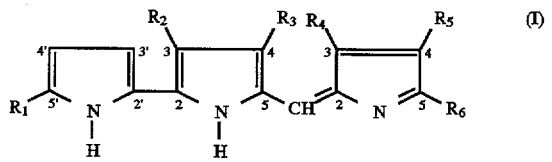

wherein $R_1$ represents hydrogen, phenyl, $C_1$–$C_{20}$ alkyl or $C_2$–$C_{20}$ alkenyl, wherein the alkyl and alkenyl groups are unsubstituted or substituted by 1 to 3 substituents chosen independently from halogen, $C_1$–$C_6$ alkoxy, hydroxy, aryl and aryloxy;

$R_2$ represents hydrogen, $C_1$–$C_6$ alkyl, cyano, carboxy or ($C_1$–$C_6$ alkoxy)carbonyl;

$R_3$ represents halogen, hydroxy or $C_1$–$C_{11}$ alkoxy unsubstituted or substituted by phenyl;

$R_4$ represents hydrogen, $C_1$–$C_6$ alkyl or phenyl;

each of $R_5$ and $R_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups are unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkyl-carbamoyl, arylcarbamoyl and —$CONR_cR_d$ in which each of $R_c$ and $R_d$ independently is hydrogen or $C_1$–$C_6$ alkyl or $R_c$ and $R_d$, taken together with the nitrogen atom to which they are linked, form a morpholino or piperidino ring;

or two of $R_4$, $R_5$ and $R_6$ taken together form a $C_4$–$C_{12}$ polymethylene chain, which is unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups are in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl;

or a pharmaceutically acceptable salt thereof; and wherein when at the same time $R_3$ is methoxy and $R_1$, $R_2$, $R_4$ and $R_5$ are hydrogen, then $R_6$ is other than hydrogen, $C_1$–$C_9$ alkyl, undecyl or dodecyl; and wherein when at the same time $R_3$ is methoxy and $R_1$, $R_2$, $R_4$ and $R_6$ are hydrogen, then $R_5$ is other than n-undecyl; and wherein when at the same time $R_3$ is methoxy, and $R_1$ and $R_2$ are hydrogen, and $R_4$ and $R_6$ are methyl, then $R_5$ is other than hydrogen or alkyl; and wherein when at the same time $R_3$ is methoxy and $R_1$, $R_2$ and $R_5$, are hydrogen, then $R_4$ and $R_6$, taken together, are other than an α-alkyl-nonamethylene, α-ethyl-alkylene, or α-butylheptamethylene chain; and wherein when at the same time $R_3$ is methoxy, $R_6$ is methyl and $R_1$, $R_2$ and $R_4$ are hydrogen, then $R_5$ is other than alkyl; and wherein when at the same time $R_3$ is methoxy and $R_1$, $R_2$ and $R_4$ are hydrogen, then $R_5$ and $R_6$, taken together, are other than α-butyl-alkylmethylene or α-alkyl-heptamethylene chain;

or $R_5$ being methyl, then $R_6$ is other than n-pentyl; or $R_5$ being ethyl, then $R_6$ is other than n-butyl; and wherein when at the same time $R_3$ is hydroxy, $R_1$, $R_2$ and $R_4$ are hydrogen and $R_6$ is methyl, then $R_5$ is other than alkyl; and wherein when at the same time $R_3$ is methoxy, $R_1$ and $R_2$ are hydrogen and $R_6$ is methyl, then $R_4$ and $R_5$, taken together, are other than an α-methyl-tetra-methylene or β-methyl-tetramethylene chain; or $R_4$ being n-propyl, then $R_5$ is other than n-heptyl; and wherein when at the same time $R_1$ and $R_2$ are hydrogen, $R_3$ is methoxy, $R_5$ is ethyl and $R_6$ is methyl, $R_4$ is other than alkyl; and wherein when at the same time $R_1$ and $R_2$ are hydrogen, $R_3$ is methoxy, $R_4$ is methyl and $R_5$ is ethyl, $R_6$ is other than $C_2$–$C_9$ alkyl; and wherein when at the same time $R_3$ is methoxy $R_1$, $R_2$, and $R_4$ are hydrogen, and $R_5$ is pentyl, then $R_6$ is other than $C_2$–$C_9$ alkyl;

when at the same time $R_3$ is hydroxy $R_1$, $R_2$, and $R_4$ are hydrogen, and $R_5$ is $C_5H_{11}$, then $R_6$ is other than $C_2$–$C_9$ alkyl;

when at the same time $R_3$ is methoxy $R_1$, $R_2$, and $R_4$ are hydrogen, and $R_5$ is $(CH_2)_5$—Me, then $R_6$ is other than $C_2$–$C_9$ alkyl;

when at the same time $R_3$ is methoxy $R_1$, $R_2$, and $R_4$ are hydrogen, and $R_5$ is n-heptyl, then $R_6$ is other than $C_2$–$C_9$ alkyl;

when at the same time $R_3$ is methoxy $R_1$, $R_2$, and $R_4$ are hydrogen, and $R_5$ is $(CH_2)_{10}$—Me, then $R_6$ is other than $C_2$–$C_9$ alkyl.

18. A pharmaceutical composition comprising a pharmaceutically acceptable carrier and/or diluent and as an active principle a compound of formula (I) as defined in claim 17, or a salt thereof.

19. A 5-[2H-pyrrol-2-ylidene)methyl]-2,2'-bi-1H-pyrrole compound having the following formula (I)

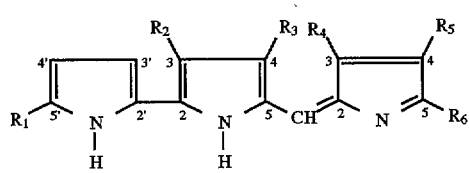

wherein

- $R_1$ represents hydrogen, phenyl, $C_1$–$C_{20}$ alkyl or $C_2$–$C_{20}$ alkenyl, wherein the alkyl and alkenyl groups are unsubstituted or substituted by 1 to 3 substituents chosen independently from halogen, $C_1$–$C_6$ alkoxy, hydroxy, aryl and aryloxy;
- $R_2$ represents hydrogen, $C_1$–$C_6$ alkyl, cyano, carboxy or ($C_1$–$C_6$ alkoxy)carbonyl;
- $R_3$ represents $C_1$–$C_{11}$ alkoxy substituted by phenyl;
- $R_4$ represents hydrogen, $C_1$–$C_6$ alkyl or phenyl;
- each of $R_5$ and $R_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups are unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkyl-carbamoyl, arylcarbamoyl and —$CONR_cR_d$ in which each of $R_c$ and $R_d$ independently is hydrogen or $C_1$–$C_6$ alkyl or $R_c$ and $R_d$, taken together with the nitrogen atom to which they are linked, form a morpholino or piperidino ring;
- or two of $R_4$, $R_5$ and $R_6$ taken together form a $C_4$–$C_{12}$ polymethylene chain, which is unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups are in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_2$ alkyl;

or a pharmaceutically acceptable salt thereof.

20. A pharmaceutical composition comprising a pharmaceutically acceptable carrier and/or diluent and as an active principle a compound as recited in claim 19, or a salt thereof.

21. 4-benzyloxy-5-[(5-undecyl-2H-pyrrol-2-ylidene)methyl]-2,2'-bi-1H-pyrrole, or a salt thereof.

22. A pharmaceutical composition comprising a pharmaceutically acceptable carrier and/or diluent and as an active principle a compound as recited in claim 21, or a salt thereof.

23. 4-methoxy-5-[(5-phenethyl-2H-pyrrol-2-ylidene)methyl]-2,2'-bi-1H-pyrrole, or a salt thereof.

24. A pharmaceutical composition comprising a pharmaceutically acceptable carrier and/or diluent and as an active principle a compound as recited in claim 23, or a salt thereof.

25. 4-butoxy-5-[(5-undecyl-2H-pyrrol-2-ylidene)methyl]-2,2'-bi-1H-pyrrole, or a salt thereof.

26. A pharmaceutical composition comprising a pharmaceutically acceptable carrier and/or diluent and as an active principle a compound as recited in claim 25, or a salt thereof.

27. 4-methoxy-5-[(5-decyl-2H-pyrrol-2-ylidene)methyl]-2,2'-bi-1H-pyrrole, or a salt thereof.

28. A pharmaceutical composition comprising a pharmaceutically acceptable carrier and/or diluent and as an active principle a compound as recited in claim 27, or a salt thereof.

29. 4-methoxy-5-[(5-pentadecyl-2H-pyrrol-2-ylidene)methyl]-2,2'-bi-1H-pyrrole, or a salt thereof.

30. A pharmaceutical composition comprising a pharmaceutically acceptable carrier and/or diluent and as an active principle a compound as recited in claim 29, or a salt thereof.

31. 4-ethoxy-5-[(5-undecyl-2H-pyrrol-2-ylidene)methyl]-2,2'-bi-1H-pyrrole, or a salt thereof.

32. A pharmaceutical composition comprising a pharmaceutically acceptable carrier and/or diluent and as an active principle a compound as recited in claim 31, or a salt thereof.

33. 4-methoxy-5-[(5-tridecyl-2H-pyrrol-2-ylidene)methyl]-2,2'-bi-1H-pyrrole, or a salt thereof.

34. A pharmaceutical composition comprising a pharmaceutically acceptable carrier and/or diluent and as an active principle a compound as recited in claim 33, or a salt thereof.

35. 4-ethoxy-5-[(5-tridecyl-2H-pyrrol-2-ylidene)methyl]-2,2'-bi-1H-pyrrole, or a salt thereof.

36. A pharmaceutical composition comprising a pharmaceutically acceptable carrier and/or diluent and as an active principle a compound as recited in claim 35, or a salt thereof.

37. 4-amyloxy-5-[(5-undecyl-2H-pyrrol-2-ylidene)methyl]-2,2'-bi-1H-pyrrole, or a salt thereof.

38. A pharmaceutical composition comprising a pharmaceutically acceptable carrier and/or diluent and as an active principle a compound as recited in claim 37, or a salt thereof.

39. A method of treating a mammal in need of an immunomodulating agent, said method comprising administering to said mammal an effective amount of 4-benzyloxy-5-[(5-undecyl-2H-pyrrol-2-ylidene)methyl]-2,2'-bi-1H-pyrrole, or a salt thereof.

40. A method of treating a mammal in need of an immunomodulating agent, said method comprising administering to said mammal an effective amount of a compound selected from the group consisting of:

4-ethoxy-5-[(5-undecyl-2H-pyrrol-2-ylidene)methyl]-2,2'-bi-1H-pyrrole;

4-methoxy-5-[(5-tridecyl-2H-pyrrol-2-ylidene)methyl]-2,2'-bi-1H-pyrrole;

4-ethoxy-5-[(5-tridecyl-2H-pyrrol-2-ylidene)methyl]-2,2'-bi-1H-pyrrole;

4-butoxy-5-[(5-undecyl-2H-pyrrol-2-ylidene)methyl]-2,2'-bi-1H-pyrrole;

4-amyloxy-5-[(5-undecyl-2H-pyrrol-2-ylidene)methyl]-2,2'-bi-1H-pyrrole;

4-methoxy-5-[(5-decyl-2H-pyrrol-2-ylidene)methyl]-2,2'-bi-1H-pyrrole;

4-methoxy-5-[(5-pentadecyl-2H-pyrrol-2-ylidene)methyl]-2,2'-bi-1H-pyrrole; and 4-methoxy-5-[(5-phenethyl-2H-pyrrol-2-ylidene)methyl]-2,2'-bi-1H-pyrrole, and salts of said compounds.

* * * * *